United States Patent
Mousa et al.

(10) Patent No.: US 11,723,888 B2
(45) Date of Patent: Aug. 15, 2023

(54) POLYMER CONJUGATED THYROINTEGRIN ANTAGONISTS

(71) Applicant: NanoPharmaceuticals, LLC, Troy, NY (US)

(72) Inventors: Shaker A. Mousa, Wynantskill, NY (US); Bruce A. Hay, Niskayuna, NY (US); Ozlem Ozen Karakus, Glenmont, NY (US)

(73) Assignee: NANOPHARMACEUTICALS LLC, Troy, NY (US)

( * ) Notice: Subject to any disclaimer, the term of this patent is extended or adjusted under 35 U.S.C. 154(b) by 0 days.

(21) Appl. No.: 17/546,328

(22) Filed: Dec. 9, 2021

(65) Prior Publication Data
US 2023/0181501 A1   Jun. 15, 2023

(51) Int. Cl.
A61K 31/192   (2006.01)
A61K 47/60   (2017.01)

(52) U.S. Cl.
CPC ............ *A61K 31/192* (2013.01); *A61K 47/60* (2017.08)

(58) Field of Classification Search
CPC .............................. A61K 31/495; A61P 43/00
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,208,483 A | 6/1980 | Lee |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,207,665 B1 | 3/2001 | Bauman et al. |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,596,712 B2 | 7/2003 | Zasloff et al. |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Renato |
| 6,936,274 B2 | 8/2005 | Hanshew, Jr. |
| 7,166,155 B2 | 1/2007 | Takeshi |
| 7,358,085 B2 | 4/2008 | Zhang et al. |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Davis et al. |
| 8,802,240 B2 | 8/2014 | Davis et al. |
| 9,180,107 B2 | 11/2015 | Mousa et al. |
| 9,198,887 B2 | 12/2015 | Mousa et al. |

(Continued)

FOREIGN PATENT DOCUMENTS

| | | |
|---|---|---|
| CA | 2673133 | 11/2008 |
| CN | 1126589 | 7/1996 |

(Continued)

OTHER PUBLICATIONS

F. Kawai, Microbial degradation of polyethers, Appl Microbiol Biotechnol (2002) 58:30-38, DOI 10.1007/s00253-001-0850-2 (Year: 2002).*

Mandelin et al., "Extracellular and Intracellular Mechanisms That Mediate the Metastatic Activity of Exogenous Osteopontin", Cancer, 115:1753-1764 (2009) 12 pages.

Mangale et al., "Identification of genes regulated by an interaction between αvβ3 integrin and vitronectin in murine decidua", Reprod. Fertil. Dev., 20:311-319 (2008) 10 pages.

(Continued)

*Primary Examiner* — Sahar Javanmard

(74) *Attorney, Agent, or Firm* — Schmeiser, Olsen & Watts, LLP

(57) ABSTRACT

Chemical compounds/compositions, methods of synthesis, and methods of use are provided. The compounds/compositions are directed toward thyrointegrin antagonists directly conjugated to a polymer. The compounds/compositions may further comprise an additional substituent also conjugated to the polymer. The compounds/compositions may demonstrate antiangiogenic effect and efficacy against conditions, particularly cancers.

13 Claims, 23 Drawing Sheets

(13 of 23 Drawing Sheet(s) Filed in Color)

(56) References Cited

U.S. PATENT DOCUMENTS

| | | |
|---|---|---|
| 9,220,788 B2 | 12/2015 | Davis et al. |
| 9,272,049 B2 | 3/2016 | Alexander-Bridges et al. |
| 9,289,395 B2 | 3/2016 | Davis et al. |
| 9,498,536 B2 | 11/2016 | Mousa et al. |
| 9,539,345 B2 | 1/2017 | Kim et al. |
| 9,579,300 B2 | 2/2017 | Mousa et al. |
| 9,750,709 B2 | 9/2017 | Mousa et al. |
| 9,839,614 B2 | 12/2017 | Mousa et al. |
| 10,130,686 B2 | 11/2018 | Mousa et al. |
| 10,201,616 B2 | 2/2019 | Mousa et al. |
| 10,328,043 B1 | 6/2019 | Mousa et al. |
| 10,961,204 B1 | 3/2021 | Mousa et al. |
| 11,077,082 B2 | 8/2021 | Mousa et al. |
| 2001/0021763 A1 | 9/2001 | Harris |
| 2001/0023254 A1 | 9/2001 | McElroy |
| 2001/0046521 A1 | 11/2001 | Zasloff et al. |
| 2002/0049247 A1 | 4/2002 | Chen |
| 2002/0132205 A1 | 9/2002 | Faour |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0104999 A1 | 6/2003 | Iozzo |
| 2003/0138557 A1 | 7/2003 | Allison |
| 2003/0143727 A1 | 7/2003 | Chang |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |
| 2004/0033259 A1 | 2/2004 | Hanshew, Jr. et al. |
| 2004/0063781 A1 | 4/2004 | Pelcman et al. |
| 2004/0208844 A1 | 10/2004 | Ignatious |
| 2004/0219668 A1 | 11/2004 | Frei et al. |
| 2005/0124862 A1 | 6/2005 | Mousa et al. |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0266393 A1 | 12/2005 | Baxter et al. |
| 2005/0272817 A1 | 12/2005 | Heino |
| 2006/0166303 A1 | 7/2006 | Spanuth |
| 2006/0210539 A1 | 9/2006 | Zhang |
| 2006/0216251 A1 | 9/2006 | Morariu |
| 2007/0117841 A1 | 5/2007 | Ozes et al. |
| 2007/0190160 A1 | 8/2007 | Turos et al. |
| 2008/0081074 A1 | 4/2008 | Gu et al. |
| 2008/0124280 A1 | 5/2008 | Mousa et al. |
| 2008/0193377 A1 | 8/2008 | Line et al. |
| 2008/0199850 A1 | 8/2008 | Sutter et al. |
| 2009/0022806 A1 | 1/2009 | Mousa et al. |
| 2009/0175862 A1 | 7/2009 | Silverio et al. |
| 2009/0197240 A1 | 8/2009 | Fishman et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0112079 A1 | 5/2011 | Thomas et al. |
| 2011/0142941 A1 | 6/2011 | Davis et al. |
| 2012/0258069 A1 | 10/2012 | Alexander-Bridges et al. |
| 2012/0315320 A1 | 12/2012 | Davis et al. |
| 2013/0224115 A1 | 8/2013 | Wang et al. |
| 2014/0044646 A1 | 2/2014 | Li et al. |
| 2014/0072635 A1 | 3/2014 | Mousa et al. |
| 2014/0072646 A1 | 3/2014 | Mousa et al. |
| 2014/0170066 A1 | 6/2014 | Rajopadhye et al. |
| 2014/0199375 A1 | 7/2014 | Mousa et al. |
| 2014/0199376 A1 | 7/2014 | Mousa et al. |
| 2014/0294931 A1 | 10/2014 | Mousa et al. |
| 2015/0139934 A1 | 5/2015 | Mousa et al. |
| 2015/0238631 A1 | 8/2015 | Kim et al. |
| 2016/0178615 A1 | 6/2016 | Alexander-Bridges et al. |
| 2016/0199309 A1 | 7/2016 | Mousa et al. |
| 2016/0348052 A1 | 12/2016 | Lin et al. |
| 2017/0080058 A1 | 3/2017 | Mousa et al. |
| 2017/0128425 A1 | 5/2017 | Marks et al. |
| 2017/0348425 A1 | 12/2017 | Mousa et al. |
| 2017/0348428 A1 | 12/2017 | Mousa et al. |
| 2019/0111145 A1 | 4/2019 | Mousa et al. |
| 2019/0314314 A1 | 10/2019 | Mousa et al. |

FOREIGN PATENT DOCUMENTS

| | | | |
|---|---|---|---|
| CN | 104530417 A | 4/2015 | |
| EP | 2954933 A1 | 12/2015 | |
| JP | 04356184 A | 12/1992 | |
| JP | 2010513526 A | 4/2010 | |
| JP | 2012520136 A | 9/2012 | |
| KR | 100830889 B1 | 5/2008 | |
| RU | 2559526 C2 | 8/2015 | |
| WO | 9500135 | 1/1995 | |
| WO | 9640048 | 12/1996 | |
| WO | 9833942 | 8/1998 | |
| WO | 9856771 | 12/1998 | |
| WO | 9951638 | 10/1999 | |
| WO | 9958119 A1 | 11/1999 | |
| WO | 9959548 A1 | 11/1999 | |
| WO | 9962549 | 12/1999 | |
| WO | 0064431 A1 | 11/2000 | |
| WO | 0078815 A1 | 12/2000 | |
| WO | 0113031 A2 | 2/2001 | |
| WO | 0113936 A1 | 3/2001 | |
| WO | 0176589 A1 | 10/2001 | |
| WO | 0203914 A2 | 1/2002 | |
| WO | 0249501 A2 | 6/2002 | |
| WO | 02060389 A2 | 8/2002 | |
| WO | 03075741 A2 | 9/2003 | |
| WO | 2004013728 A2 | 2/2004 | |
| WO | 2004069201 A2 | 8/2004 | |
| WO | 2005027895 A2 | 3/2005 | |
| WO | 2006003014 A2 | 1/2006 | |
| WO | 2006031922 A2 | 3/2006 | |
| WO | 200735612 A2 | 3/2007 | |
| WO | 2008051291 A2 | 5/2008 | |
| WO | 2008140507 A2 | 11/2008 | |
| WO | 2010075332 A1 | 7/2010 | |
| WO | 2010120506 A1 | 10/2010 | |
| WO | 2010148007 A2 | 12/2010 | |
| WO | 2012009425 A2 | 1/2012 | |
| WO | 2015074050 A1 | 5/2015 | |
| WO | 2016004043 | 1/2016 | |
| WO | 2017214299 | 12/2017 | |
| WO | WO-2017214299 A1 * | 12/2017 | ............ A61K 31/19 |

OTHER PUBLICATIONS

Markgraf et al., "Sensorimotor and cognitive consequences of middle cerebral artery occlusion in rats", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.

Masson-Gadais et al., "Integrin αvβ3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothyroidism", Cancer Res., 39:2371-2375 (1979) 5 pages.

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

(56) References Cited

OTHER PUBLICATIONS

Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.
Moeller et al., "Thyroid hormone mediated changes in gene expression can be initiated by cytosolic action of the thyroid hormone receptor beta through the phosphatidylinositol 3-kinase pathway", Nuclear Receptor Signaling, 4:E020 (2006) 4 pages.
Mohamed et al., "Wound healing properties of cimetidine in vitro", Drug Intell. Clin. Pharm., 20(12):973-975 (1986) 4 pages.
Monferran et al., "αvβ3 and αvβ5 integrins control glioma cell response to ionising radiation through ILK and RhoB", Int. J. Cancer, 123:357-364 (2008) 8 pages.
Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.
Moreno et al., "Metabolic Effects of Thyroid Hormone Derivatives", Thyroid, 18(2):239-253 (2008) 15 pages.
Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18(2):239-253 (2008) 15 pages.
Mousa et al., "Cellular and Molecular Mechanisms of Nicotine's Pro-Angiogenesis Activity and Its Potential Impact on Cancer", J. Cell. Biochem., 97:1370-1378 (2006) 9 pages.
Mousa et al., "Discovery of Pro-Angiogenic Effects of Nicotine's Pro-Angiogenesis Activity and Its Potential Impact on Cancer", J Cell. Biochem., 97:1370-1378 (2006) Abstract Only. 3 pages.
Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.
Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.
Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.
Mousa et al., "The Proangiogenic Action of Thyroid Hormone Analogue GC-1 Is Initiated at an Integrin", J. Cardiovasc. Pharmacol., 46(3):356-360 (2005) 6 pages.
Mousa, et al., "Pro-angiogenesis action of thyroid hormone and analogs in a three-dimensional in vitro microvascular endothelial sprouting model", Int. Angiol., 25(4):407-413 (2006).
Mousa, S.A., "Mechanisms of Angiogenesis: Potential Therapeutic Targets", in Angiogenesis Inhibitors and Stimulators: Potential Therapeutic Implications, Landes Bioscience, Georgetown, Texas, Chapter I, pp. 1-12 (2000) 14 pages.
Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.
Muller et al., "The Double Life of the Ku Protein: Facing the DNA Breaks and the Extracellular Environment", Cell Cycle, 4(3):438-441 (2005) 4 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.
Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.
Nehls et al., "A Novel Micorcarrier-Based in Vitro Assay for Rapid and Reliable Quantification of Three-Dimensional Cell Migration and Angiogenesis", Microvasc. Res., 50(3):311-322 (1995) 12 pages.

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.
Newcomb et al., "Radiation Sensitivity of GL261 Murine Glioma Model and Enhanced Radiation Response by Flavopiridol", Cell Cycle., 5(1):93-99 (2006) 7 pages.
Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.
Nilsson et al., "Evidence for Multiple Thyroxine-binding Sites in Human Prealbumin", J. Biol. Chem., 246(19):6098-6105 (1971) 8 pages.
Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.
Oak et al., "Antiangiogenic properties of natural polyphenols from red wine and green tea", J. Nutr. Biochem., 16:1-8 (2005) 8 pages.
Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.
Pages et al., "Signaling Angiogenesis via p42/p44 MAP Kinase Cascade", Ann. N.Y. Acad., Sci., 902:187-200 (2000) 14 pages.
Painter et al., "Membrane initiation of DNA synthesis", Nature, 270:543 (1977) 1 page.
Panter et al., "Pretreatment with NMDA antagonists limits release of excitatory amino acids following traumatic brain injury", Neurosci. Lett., 136(2):165-168 (1992) 4 pages.
Panyam, et al., "Biodegradable nanoparticles for drug and gene delivery to cells and tissues", Advanced Drug Delivery Reviews, 55: 329-347 (2009) 19 pages.
Pardridge, W.M., "Receptor-Mediated Peptide Transport through the Blood-Brain Barrier", Endocrine Rev., 7(3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharmacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett., 20(11):3394-3398 (2010) 5 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.
Brooks et al., "Antintegrin αvβ3 blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
Burgman et al., "Effect of Inhibitors of Poly(ADP-Ribose)Polymerase on the Radiation Response of HeLa S3 Cells", Radiat. Res., 119:380-386 (1989) 7 pages.

(56) References Cited

OTHER PUBLICATIONS

Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (1992) 5 pages.
Charness et al., "Ethanol Increases the Expression of Functional Delta-Opioid Receptors in Neuroblastoma x Glioma NG108-15 Hybrid Cells", J. Biol. Chem., 261(7):3164-3169 (1986) 6 pages.
Charo et al., "The Vitronectin Receptor αvβ3 Binds Fibronectin and Acts in Concert with α5β1 in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, dated Nov. 30, 2007, cited CN 1126589. 6 pages.
Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with αvβ3 integrin", Steroids, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "αvβ3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database BIOSIS [Online], Accession No. PREV20040016159, Abstract, Mousa et al., "Discovery of pro-angiogenic effects of thyroid hormone and analogs", Blood, 102(11):77b-78b (2003) 1 page. Same @ 221 and 365.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Reviews of Endocrinology and Metabolism, 1(6):753-761 (2006) 10 pages.

Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane but Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573(1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Oncol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother., 46(2):464-470 (2002) 7 pages.
Dupont et al., "Antiangiogenic and antimetastatic properties of Neovastat (Æ 941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Hudlicka et al., "Factors involved in capillary growth in the heart", Mol. Cell. Biochem, 147:57-68 (1995) 12 pages.
Igarashi et al., "Techniques Supporting Angiogenesis Therapy 2: DDS Technique Supporting Regenerative Medicine." Inflamm. Immun. 10.6(2002):652-658 7 pages.
Illario et al., "Fibronectin-Induced Proliferation in Thyroid Cells is Mediated by αvβ3 Integrin through Ras/Raf-1/MEK/ERK and Calcium/CaMKII Signals", J. Clin. Endocrinol. Metab., 90(5):2865-2873 (2005) 9 pages.

(56) References Cited

OTHER PUBLICATIONS

Ingerman-Wojenski et al., "Evaluation of electrical aggregometry: comparison with optical aggregometry, secretion of ATP, and accumulation of radiolabeled platelets", J. Lab. Clin. Med., 101(1):44-52 (1983) 10 pages.

Iwata et al., "A new, convenient method for the preparation of 4-[18F]fluorobenzyl halides", Applied Radiation and Isotopes, 52(1):87-92 (2000) 7 pages.

Jain, K.K., "Strategies and technologies for drug delivery systems", Tips, 19:155-157 (1998) 5 pages.

Janssen et al., "Pathogenesis of Spinal Cord Injury and Newer Treatments—A Review", Spine, 14(1):23-32 (1989) 11 pages.

Jeffrey et al., "The preparation and characterisation of poly(lactide-co-glycolide) microparticles. 1. Oil-in-water emulsion solvent evaporation", Int. J. Pharm., 77:169-175 (1991) 7 pages.

Jonker et al., "Cetuximab for the Treatment of Colorectal Cancer", N. Engl. J. Med., 357(20):2040-2048 (2007) 9 pages.

Jordan et al., "Thyroid Status is a Key Modulator of Tumor Oxygenation: Implication for Radiation Therapy", Radiat. Res., 168:428-432 (2007) 5 pages.

Kalofonos et al., "Monoclonal Antibodies in the Management of Solid Tumors", Curr. Top. Med. Chem., 6:1687-1705 (2006) 19 pages.

Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.

Kastan et al., "A Mammalian Cell Cycle Checkpoint Pathway Utliziing P53 and GADD45 is Defective in Ataxia-Telangiectasia", Cell. 71:587-597 (1992) 11 pages.

Kawasuji et al., Jap. Circ. J., 63(Suppl. 1):65 (1999) Japanese Abstract Only. 3 pages.

Kerr et al., "Novel Small Molecule αv Integrin Antagonists: Comparative Anti-Cancer Efficacy with Known Angiogenesis Inhibitors", Anticancer Res., 19:959-968 (1999).

Kerr et al., "Small molecule αV integrin antagonists: novel anti-cancer agents", Exp. Opin. Invest. Drugs, 9 (6):1271-1279 (2000) 9 pages.

Kim et al., "Regulation of Angiogenesis in Vivo, by Ligation of Integrin α5β1 with the Central Cell-Binding Domain of Fibronectin", Am. J. Pathol., 156(4): 1345-1362 (2000) 18 pages.

Kim et al., "Soluble Flt-1 gene delivery using PEI-g-PEG-RGD conjugate for anti-angiogenesis", J. Control Release, 106:224-234 (2005) 11 pages.

Kimelberg, H.K., "Astrocytic Edema in CNS Trauma", J. Neurotrauma, 9(Suppl. 1):S71-S81 (1992) 12 pages.

Kitevska et al., "Caspase-2: controversial killer or checkpoint controller?", Apoptosis, 14:829-848(2009) 20 pages.

Kleczkowska et al., "Differential poly(ADP-ribose) metabolism in repair-proficient and repair-deficient murine lymphoma cells", Mut. Res., 235:93-99 (1990) 7 pages.

Klunk et al., "Development of Small Molecule Probes for the Beta-Amyloid Protein of Alzheimer's Disease", Neurobiol. Aging, 15(6):691-698 (1994) 8 pages.

Kobayashi et al., "Drug Delivery Catheter." Surg. Front. 9.1(2002):55-57 3 pages.

Konno et al., "Antiogenetic therapy for carcinoma", Igaku No Ayumi, 194(10): 824-828 (2000) 5 pages.

Koutras et al., "Antiproliferative effect of exemestane in lung cancer cells", Mol. Cancer, 8(1):109 (2009) 12 pages.

Koyama et al., "Recent Status and Future Perspectives in Therapeutic Angiogenesis", Prog. Med., 22(12):3070-3076 (2002) (English Abstract) 7 pages.

Kramer et al., "Human Microvascular Endothelial Cells Use β1 and β3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.

Kuroki et al., "Diabetic retinopathy—The mechanisms of the ocular neovascularization of the development of anti-angiogenic drugs—", Nippon Rinsho, 57(3):584-589 (1999) (English Abstract Only) 6 pages.

Kwok et al., "Differences in EGF rated radiosensitisation of human squamous carcinoma cells with high and low numbers of EGF receptors", Br. J. Cancer, 64:251-254 (1991) 4 pages.

Lameloise et al., "Differences between the effects of thyroxine and tetraiodothyroacetic acid on TSH suppression and cardiac hypertrophy", Eur. J. Endocrinol., 144:145 154 (2001) 10 pages.

Lawler et al., "Cell Attachment to Thrombospondin: The Role of ARG-GLY-ASP, Calcium and Integrin Receptors", J. Cell Biol., 107(6 Pt. 1): 2351-2361 (1988) 11 pages.

Letterio et al., "Maternal Rescue of Transforming Growth Factor-β1 Null Mice", Science, 264:1936-1938 (1994) 4 pages.

Li et al., "Requirement of hypoxia-inducible factor-1α down-regulation in mediating the antitumor activity of the anti-epidermal growth factor receptor monoclonal antibody cetuximab", Mol. Cancer Ther., 7(5):1207-1217 (2008) 11 pages.

Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.

Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.

Lin et al., "Integrin αvβ3 contains a receptor site for resveratrol", FASEB J., 20(10): 1742-1744 (2006) 3 pages.

Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.

Lin et al., "Resveratrol Causes COX-2- and p53-Dependent Apoptosis in Head and Neck Squamous Cell Cancer Cells", J. Cell Biochem., 104:2131-2142 (2008) 12 pages.

Lin et al., "Resveratrol Induced Serine Phosphorylation of p53 Causes Apoptosis in a Mutant p53 Prostate Cancer Cell Line", J. Urol., 168:748-755 (2002) 8 pages.

Lin et al., "Resveratrol is pro-apoptotic and thyroid hormone is anti-apoptotic in glioma cells: both actions are integrin and ERK mediated", Carcinogenesis, 29(1):62-69 (2008) 8 pages.

Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.

Lin et al., "Thyroid hormone is a MAPK-dependent growth factor for thyroid cancer cells and is anti-apoptotic", Steroids, 72:180-187 (2007) 8 pages.

Liu et al., "Calcineurin Is a Common Target of Cyclophilin-Cyclosporin A and FKBP-FK506 Complexes", Cell, 66:807-815 (1991) 9 pages.

Lorger et al., "Activation of tumor cell integrin αvβ3 controls angiogenesis and metastatic growth in the brain", Proc. Natl. Acad. Sci. U.S.A., 106(26):10666-10671 (2009) 7 pages.

Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.

Luidens et al., "Thyroid hormone and angiogenesis", Vascular Pharmacology, 52(3-4): 142-145 (2010) 4 pages.

Lyons et al., "The Expression of an N-CAM Serum Fragment is Positively Correlated with Severity of Negative Features in Type II Schizophrenia", Biol. Psychiatry, 23:769-775 (1988) 7 pages.

Ma, et al., "Use of Encapsulated Single Chain Antibodies for Induction of Anti-Idiotypic Humoral and Cellular Immune Responses", J. Pharm. Sci., 87:1375-1378 (1998). 4 pages.

Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

(56) References Cited

OTHER PUBLICATIONS

Faden et al., "Endogenous Opioid Immunoreactivity in Rat Spinal Cord Following Traumatic Injury", Ann. Neurol., 17(4):386-390 (1985) 5 pages.
Faden, A.I., "Experimental Neurobiology of Central Nervous System Trauma", Crit. Rev. Neurobiol., 7(3-4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of $\alpha v/\beta 3$ mRNA by Fibrin", J. Invest. Dermatol, 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521(1-2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death In Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110δ Catalytic Component of Phosphatidylinositol 3'-Kinase, IC486068, Enhances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin $\alpha v\beta 3$ in Small Blood Vessels of Glioblastoma Tumors", J. Neuropath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression profiling predicts clinical outcome of prostate cancer", J. Clin. Invest., 113(6):913-923 (2004) 11 pages.
Glinsky et al., Microarray analysis identifies a death-from-cancer signature predicting therapy failure in patients with multiple types of cancer, J. Clin. Invest., 115(6):1503-1521 (2005) 19 pages.
Glinsky et al., Microarray Analysis of Xenograft-Derived Cancer Cell Lines Representing Multiple Experimental Models of Human Prostate Cancer, Mol. Carcinog., 37:209-221 (2003) 13 pages.
Goldstein et al., "Influence of Lesion Size and Location on Amphetamine-Facilitated Recovery of Beam-Walking in Rats", Behav. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for congenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation of β-Catenin by a Novel Nongenomic Action of Thyroid Hormone β Receptor", Mol. Cell. Biol., 28(14):4598-4608 (2008) 11 pages.
Hahn et al., "Plateau-phase cultures of mammalian cells: An in vitro model for human cancer", Curr. Top. Radiat. Res. Q., 8:39-83 (1972) 45 pages.
Halks-Miller et al., "CCR1 Immunoreactivity in Alzheimer's Disease Brains", Society for Neuroscience Meeting, Abstract #787.6, vol. 24 (1998) Abstract Only. 1 page.
Hansebout, R.R., "A Comprehensive Review of Methods of Improving Cord Recovery After Acute Spinal Cord Injury", in Early Management of Acute Spinal Cord Injury, pp. 181-196 (1982) 16 pages.
Hartert, H., "Blutgerinnungsstud Mit Der Thrombelastogeraphie, Einem Neuen Untersuchungsverfahren", Klinische Wochenschrift 26(37/38):577-583 (1948) German Language Only. 9 pages.
Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.
Heller et al., "Inhibition of potentially lethal damage recovery by altered pH, glucose utilization and proliferation in plateau growth phase human glioma cells", Int. J. Radiat. Biol., 66(1):41-47 (1994) 7 pages.
Hercbergs et al., "GL261 brain tumor cells: responses to single or fractionated x-irradiation with the $\alpha v\beta 3$ integrin thyroxine receptor antagonist tetrac (tetraiodothyroacetic acid)", 20th EORTC-NCI-AACR Symposium on Molecular Targets and Cancer Therapeutics, Geneva, Switzerland, Oct. 2008.
Hercbergs et al., "Propylthiouracil-induced Chemical Hypothyroidism with High-Dose Tamoxifen Prolongs Survival in Recurrent High Grade Glioma: A Phase I/II Study", Anticancer Res., 23:617-626 (2003) 10 pages.
Hercbergs, A., "The Thyroid Gland as an Intrinsic Biologic Response-Modifier in Advanced Neoplasia—A Novel Paradigm", in vivo, 10:245-247 (1996) 3 pages.
Hercbergs, et al., "Radiosensitization of GL261 glioma cells by tetraiodothyroacetic acid (tetrac)", Cell Cycle, 8(16):2586-2591 (2009) 6 pages.
Hermanson, "Modification with Synthetic Polymers", in Bioconjugate Tech., Ch. 15, Academic Press, San Diego, CA, pp. 617-618 (1996) 4 pages.
Hoff et al., "Medullary Thyroid Carcinoma", Hematol. Oncol. Cin. North Am., 21 (3):475-488 (2007) 14 pages.
Horuk et al., "Expression of Chemokine Receptors by Subsets of Neurons in the Central Nervous System", J. Immunol., 158:2882-2890 (1997) 9 pages.
Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.
Pujol et al., "Letter to the editors: Prevention of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.

(56) References Cited

OTHER PUBLICATIONS

Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acid: a cancer chemosensitizing and anticancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha v \beta 3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10(6):638-642 (2004) 5 pages.
Scanlan et al., "Selective thyromimetics: Tissue-selective thyroid hormone analogs", Curr. Opin. Drug Discov. Dev., 4(5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin αvβ3 in Gliomas Correlates with Tumor Grade and Is not Restricted to Tumor Vasculature", Brain Pathol., 18:378-386 (2008) 9 pages.
Schreiber et al., "Hormone delivery systems to the brain-transthyretin", Exp. Clin. Endocrinol. Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4):1708-1717 (2004) 10 pages.
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "αVβ3/αVβ5 integrins-FAK-RhoB: A Novel Pathway for Hypoxia Regulation in Glioblastoma", Cancer Res., 69(8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Strieth, et al., "Antiangiogenic combination tumor therapy blocking αv-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n in Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360(6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages. (50199PCT IPRP Mar. 16, 2006).
Tomanek et al., "Angiogenesis: New Insights and Therapeutic Potential", Anatomical Record (New Anat.), 261:126-135 (2000) 10 pages.
Tomanek et al., "Early Coronary Angiogenesis in Response to Thyroxine: Growth Characteristics and Upregulation of Basic Fibroblast Growth Factor", Circ. Res., 82(5):587-593 (1998) 8 pages. (50199PCT IPRP Mar. 16, 2006).
Tomanek et al., "Growth of the Coronary Vasculature in Hypertrophy: Mechanisms and Model Dependence", Cell. Mol. Bio. Res., 40(2):129-136 (1994) 8 pages. (50199PCT IPRP Mar. 16, 2006).
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.

(56) References Cited

OTHER PUBLICATIONS

"Rajabi, Mehdi et al: ""Synthesis of new analogs of tetraiodothyroacetic acid (tetrac) as novelangiogenesis inhibitors for treatment of cancer"", Bioorganic & Medicinal Chemistryletters, vol. 28, No. 7, Feb. 26, 2018 (Feb. 26, 2018), pp. 1223-1227, ISSN: 0960-894X".
European Extended Search Report for Application No. EP19785811.1 dated Dec. 10, 2021. (53227EP01).
PCT International Search Report & Written Opinion dated Aug. 5, 2021 corresponding to PCT International Application No. PCT/US 21/24294.
Non-Final Office Action (dated Sep. 20, 2021) for U.S. Appl. No. 17/340,843, filed Jun. 7, 2021.
JP Office Action (dated Sep. 21, 2021) for Patent Application No. JP20190516911—Filing Date Dec. 7, 2018.
Office Action (dated Dec. 8, 2021) for U.S. Appl. No. 15/056,522, filed Feb. 29, 2016.
Notice of Allowance (dated Jan. 26, 2022) for U.S. Appl. No. 17/340,843, dated Jun. 7, 2021.
Restriction Requirement (dated Apr. 1, 2022) for U.S. Appl. No. 17/546,328, filed Dec. 9, 2021.
Indian Office Action (dated Mar. 10, 2022) for Patent Application No. IN202047042895—Filing Date Feb. 10, 2020.
Singapore Search Report and Written Opinion dated Mar. 16, 2022 for Patent Application No. 11202009554U—Filing Date Apr. 3, 2019.
Vogus, D. R. et al., A review on engineering polymer drug conjugates to improve combination chemotherapy. Current Opinion in Colloid & Interface Science, Aug. 24, 2017, vol. 31, pp. 75-85; Whole document especially for pp. 77-81, section 3. Applications of combination treatment with PDCs.
Villaverde, G. et al., New targeting agent in selective drug delivery nanocarriers for treating neuroblastoma. Journal of Materials Chemistry B, May 14, 2015, vol. 3, No. 24, pp. 4831-4842 Section Results and discussion, fig. 1-6, the 6th paragraph of the section; Introduction.
Advisory Action (dated Feb. 27, 2008) for U.S. Appl. No. 10/943,072, filed Sep. 14, 2004.
Office Action (dated May 15, 2008) for U.S. Appl. No. 10/943,072, filed Sep. 14, 2004.
Office Action (dated Jan. 8, 2009) for U.S. Appl. No. 10/943,072, filed Sep. 14, 2004.
Office Action (dated Jun. 22, 2009) for U.S. Appl. No. 10/943,072, filed Sep. 14, 2004.
Notice of Allowance (dated Dec. 11, 2009) for U.S. Appl. No. 10/943,072, filed Sep. 14, 2004.
Office Action (dated Mar. 24, 2015) for U.S. Appl. No. 13/975,725, filed Aug. 26, 2013.
Final Office Action (dated Oct. 9, 2015) for U.S. Appl. No. 13/975,725, filed Aug. 26, 2013.
Advisory Action (dated Dec. 31, 2015) for U.S. Appl. No. 13/975,725, filed Aug. 26, 2013.
Office Action (dated Jun. 17, 2016) for U.S. Appl. No. 13/975,725, filed Aug. 26, 2013.
Final Office Action (dated Apr. 3, 2017) for U.S. Appl. No. 13/975,725, filed Aug. 26, 2013.
Notice of Allowance (dated Jan. 31, 2018 U.S. Appl. No. 13/975,725, filed Aug. 26, 2013.
Office Action (dated May 12, 2015) for U.S. Appl. No. 14/078,713, filed Nov. 13, 2013.
Notice of Allowance (dated Aug. 3, 2015) for U.S. Appl. No. 14/078,713, filed Nov. 13, 2013.
Restriction Requirement (dated Dec. 3, 2015) for U.S. Appl. No. 14/184,889, filed Feb. 20, 2014.
Office Action (dated May 6, 2016) for U.S. Appl. No. 14/184,889, filed Feb. 20, 2014.
Notice of Allowance (dated Oct. 13, 2016) for U.S. Appl. No. 14/184,889, filed Feb. 20, 2014.
Restriction Requirement (dated Dec. 2, 2015) for U.S. Appl. No. 14/185,010, filed Feb. 20, 2014.
Office Action (dated Sep. 9, 2016) for U.S. Appl. No. 14/185,010, filed Feb. 20, 2014.
Notice of Allowance for U.S. Appl. No. 14/185,010 (dated Apr. 4, 2017).
Office Action (dated Oct. 14, 2014) for U.S. Appl. No. 14/242,041, filed Apr. 2, 2014.
Office Action (dated Jun. 11, 2015) for U.S. Appl. No. 14/242,041, filed Apr. 1, 2014.
Final Office Action (dated Oct. 16, 2015) for U.S. Appl. No. 14/242,041, filed Apr. 1, 2014.
Advisory Action (dated Jan. 21, 2016) for U.S. Appl. No. 14/242,041, filed Apr. 1, 2014.
Office Action (dated May 26, 2016) for U.S. Appl. No. 14/242,041, filed Apr. 2, 2014; (Prosection Not Cited but Prior Art References Were).
Notice of Allowance (dated Jul. 19, 2016) for U.S. Appl. No. 14/242,041, filed Apr. 1, 2014.
Restriction Requirement (dated Nov. 4, 2015) for U.S. Appl. No. 14/546,440, filed Nov. 18, 2014.
Office Action (dated Mar. 24, 2016) for U.S. Appl. No. 14/546,440, filed Nov. 18, 2014.
Office Action (dated Sep. 30, 2016) for U.S. Appl. No. 14/546,440, filed Nov. 18, 2014.
Office Action (dated Oct. 4, 2017) for U.S. Appl. No. 14/546,440, filed Nov. 18, 2014.
Notice of Allowance (dated May 3, 2018) for U.S. Appl. No. 14/546,440, filed Nov. 18, 2014.
Restriction Requirement (dated Feb. 9, 2017) for U.S. Appl. No. 15/056,522, filed Feb. 29, 2016.
Office Action (dated Jun. 13, 2018) for U.S. Appl. No. 15/056,522, filed Feb. 29, 2016.
Office Action (dated Feb. 15, 2019) for U.S. Appl. No. 15/056,522, filed Feb. 29, 2016.
Office Action (dated Jun. 11, 2018) for U.S. Appl. No. 14/903,149, filed Jan. 6, 2016.
Final Office Action (dated Mar. 13, 2019) for U.S. Appl. No. 14/903,149, filed Jan. 6, 2016.
Office Action (dated Dec. 29, 2017) for U.S. Appl. No. 15/357,818, filed Nov. 21, 2016.
Office Action (dated Apr. 20, 2018) for U.S. Appl. No. 15/357,818, filed Nov. 21, 2016.
Notice of Allowance (dated Jul. 3, 2018) for U.S. Appl. No. 15/357,818, filed Nov. 21, 2016.
Office Action (dated May 10, 2018) for U.S. Appl. No. 15/616,637, filed Jun. 7, 2017.
Notice of Allowance (dated Sep. 2, 2018) for U.S. Appl. No. 15/616,637, filed Jun. 7, 2017.
Restriction Requirement (dated Oct. 12, 2018) for U.S. Appl. No. 15/950,870, filed Apr. 11, 2018.
Office Action (dated Nov. 28, 2018) for U.S. Appl. No. 15/950,870, filed Apr. 11, 2018.
Notice of Allowance (dated Feb. 6, 2019) for U.S. Appl. No. 15/950,870, filed Apr. 11, 2018.
Restriction Requirement (dated Sep. 11, 2019) for U.S. Appl. No. 16/223,176, filed Dec. 18, 2018.
Notice of Allowance (dated Feb. 26, 2020) for U.S. Appl. No. 16/223,176, dated Dec. 18, 2018.
Application No. PCT/US19/025489, International Search Report and the Written Opinion Opinion dated May 1, 2019. 8 pages. (53227PCT).
Kawai, "Excerpt of table 1 from Biodegration of Polyethers (Polyethylene Glycol, Polypropylene Glycol, Polytetramethylene glycol, and Others)." In: "Biopolymers : [biology, chemistry, biotechnology, applications]," Jan. 15, 2005, Wiley-VCH, Weinheim [u.a.], XP55655138.
Kawai, "Biodegradation of Polyethers (Polyethylene Glycol, Polypropylene Glycol, Polytetramethylene glycol, and Others)," Biopolymers: Part 9. Miscellaneous Biopolymers and Biodegradation of Polymers, Jan. 15, 2015, XP055655101, Retrieved from the Internet: URL:https://onlinelibrary.wiley.com/doi/full/10.1002/3527600035.bpol9012 [retrieved on Jan. 7, 2020].
Extended European Search Report in related European Patent Application No. 17810954.2, dated Jan. 30, 2020; 9 pages.

(56) References Cited

OTHER PUBLICATIONS

Notice of Allowance (dated Jul. 21, 2021) for U.S. Appl. No. 17/173,561, filed Feb. 11, 2021.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel αv integrin antagonist SM256 and cis-platinum on growth of murine squamous cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Varnes et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages. (50199PCT IPRP Mar. 16, 2006).
Wang et al., "Integrin-associated Protein Stimulates α2β1-dependent Chemotaxis via Gi-mediated inhibition of Adenylate Cyclase and Extracellular-regulated Kinases", J. Cell. Biol., 147:389-399 (1999) 11 pages.
Wen et al., "Prognostic Value of EGFR and TGF-α in Early Laryngeal Cancer Treated With Radiotherapy", Laryngoscope, 106(7):884-888 (1996) 6 pages.
Werdelin et al., "Neuropeptides and neural cell adhesion molecule (NCAM) in CSF from patients with ALS", Acta Neurol. Scand., 79(3):177-181 (1989).
Wilkinson, J.H., "Synthesis of some Possible Metabolites of Thyroxine and Triiodothyronine", Biochem. J., 63:601-605 (1956) 5 pages.
Xia et al., "Chemokines/chemokine receptors in the central nervous system and Alzheimer's disease", J. NeuroVirol., 5:32-41 (1999) 11 pages.
Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.
Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "Enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Corepressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin αvβ3 Expression with 18F-FRGD2", J. Nucl. Med., 47:113-121 (2006) 9 pages.
Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.
NCI Cancer Drug Information, Cetuximab, 2006,http://www.cancer.gov/cancertopics/druginfo/cetuximab,downloaded Jul. 18, 2014.
Gu et al. 2007, Nanotoday 2:14-21.
Wood, J. et al. "Novel Antiangiogenic Effects of the u Bisphosphonate Compound Zoledronic Acid." The Journal of Pharmacology and Experimental Therapeutics, vol. 302, No. 3, 2002, pp. 1055-1061.
Park, T.G., "Bioconjugation of Biodegradable Poly (lactic'glycolic acid) to Protein, Peptide, and Anti-Cancer Drug: An Alternative Pathway for Achieving Controlled Release from Micro- and Nanoparticles." in Polymeric Drugs and Drug Delivery Systems, Ottenbrite R.M. and Kim S.W., eds., Ch. 7, pp. 101-114 (2001).
Oh, Jong Eun, et al., "Conjugation of drug to poly (D,L-lacitic-co-glycoli acid) for controlled release from biodegradable microspheres." Journal of Controlled Release 57, 269-280 (1999).
Ditsch, Nina, et al., "Thyroid Function in Breast Cancer Patients." Anticancer Research 30: 1713-1718 (2010).
Webmd.com (http://www.webmd.com/women/news/20030410/underactive-thyroid-lowers-breast-cancer). Dated Apr. 10, 2003.
Mousa, Shaker A., et al., "Tetraiodothyroacetic acid and its nanoformulation inhibit thyroid hormone stimulation of non-small cell lung cancer cells in vitro and its growth in xenografts." Lung Cancer 76; 39-45 (2012).
Leuthy, A.; et al. "autologous stem cell transplantation: leukapheresis product has anti-angiogenic effects in vivo correlating with neutrophil-derived VEGFR1" Anticancer Research, 2001, v.31, 9.3115-3124.
Mythyroid.com. "Blood tests" (Http://222.mythyroid.com/bloodtests.html) cached 2005 wayback machine.
Huang, Kuo-Shiang, et al. "Combination of Baculovirus-Mediated Gene Delivery and Packed-Bed Reactor for Scalable Production of Adeno-Associated Virus", Human Gene Therapy, Mary Ann Liebert, Inc., Publishers, US., vol. 18, No. 11. 2007, pp. 1161-1170.
Lin, Hung-Yun, et al. "Pharmacodynamic Modeling of Anti-Cancer Activity of Tetraiodotheyroacetic Acid in a Perfused Cell Culture System" Plos Computational Biology, vol. 7, N.2, 2011, p.e1001073.
Veronese, "Peptide and protein PEGylation: a review of problems and solutions" Biomaterials 22 (2001) 405-417.
Oshaghi, Ebrahim Abbasi, et al., "Role of resveratrol in the management of insulin resistance and related conditions: Mechanism of action," Critical Reviews in Clinical Laboratory Sciences, 2017. vol. 54, No. 4, pp. 27-293.
Mayo Clinic, "Multiple sclerosis—Diagnosis and treatment," URL: https://www.mayoclinic.org/diseases-conditions/multiple-sclerosis/diagnosis-treatment/drc-20350274 accessed Dec. 21, 217, 12 printed pages. (Year: 2017).
Susman, E., "Beware of Non-Aspirin NSAIDs for Kidney Cancer Patients." Genitourinary Cancers Symposium, oncology-times.com, 2016, p. 21. (Year: 2016).
European Examination Report for EP Application No. 07867073.4, dated Jul. 16, 2015. (50199CIP2EP).
Application No. PCT/US04/030583, International Preliminary Report on Patentability dated Mar. 16, 2006, 9 pates. (50199PCT).

(56) References Cited

OTHER PUBLICATIONS

Lane, N.E., et al., "Osteoarthritis year in review 2016: clinical," Osteoarthritis and Cartilage, vol. 25, 2017, pp. 209-215 (Year: 2017).
*Kennecott Corporation*, Plaintiff-Appellant v. *Kyocera International, Inc., and Kyoto Ceramic Co., Ltd.*, Defendant-Appellee. Case Decided Dec. 22, 1987. (https://law.resource.org/pub/us/case/reporterF2/835/835.F2d.1419.871151.html), accessed Jan. 15, 2016, 5 printed pages.
Application No. PCT/US11/043837, International Preliminary Report on Patentability dated Jan. 15, 2013. 5 pages. (50996PCT).
Office Action (dated Mar. 30, 2020) for U.S. Appl. No. 15/056,522, filed Feb. 29, 2016.
Restriction Requirement (dated Jul. 30, 2020) for U.S. Appl. No. 16/398,342, filed Apr. 30, 2019.
Li, Biomacromolecules 2003, 4, 1055-1067. (Year: 2003).
Ulbrich, Chem. Rev. 2016, 116, 5338-5431, published Apr. 25, 2016. (Year: 2016).
Bertolla, Carine et al., Monofunctionalizations of beta-cyclodextrin, conjugation with recognition patterns, and biological evaluation, Bioorganic & Medicinal Chemistry Letters, Elsevier Ltd., NL., vol. 18. Available online Feb. 10, 2008.
Japanese Office Action (dated Mar. 23, 2021) for Patent Application No. JP20190513717—Filing Date May 20, 2016.
Notice of Allowance (dated Mar. 31, 2021) for U.S. Appl. No. 16/398,342, filed Apr. 30, 2019.
Lala, Peeyush K. et al. "Role of nitric oxide in tumor progression: Lessons from experimental tumors", Cancer and Metastasis Reviews, Kluwer Academic Publishers, NL., vol. 17, No. 1. 1998, pp. 91-106.
Golub, T.R. et al. "Molecular Classification of Cancer: Class Discovery and Class Prediction by Gene Expression Monitoring", Science, www.sciencemag.org, US., vol. 286. 1999, pp. 531-537.
Cancer [online], [retrieved on Jul. 6, 2007]. Retrieved from the internet, URL http://www.nlm.nih.gov/medlineplus/cancer.html>.
Keith, John M. et al. "The SAR of brain penetration for a series of heteroaryl urea FAAH inhibitors", Bioorganic & Medicinal Chemistry Letters, Elsevier Ltd., NL., vol. 26. 2016, pp. 3109-3114.
Office Action (dated Oct. 31, 2019) for U.S. Appl. No. 16/223,176, filed Dec. 18, 2018.
Office Action (dated Nov. 30, 2020) for U.S. Appl. No. 16/398,342, filed Apr. 30, 2019.
U.S. Appl. No. 16/862,076, filed Apr. 29, 2020; GAU 1626; Confirmation No. 3113; Customer No. 05409.
Notice of Allowance (dated Nov. 13, 2020) for U.S. Appl. No. 16/862,076, filed Apr. 29, 2020.
Office Action (dated Apr. 7, 2021) for U.S. Appl. No. 17/173,561, filed Feb. 11, 2021.
Final Office Action (dated Dec. 30, 2020) for U.S. Appl. No. 15/056,522, filed Feb. 29, 2016.
European Patent Application No. 10 790 068.0, Office Action dated Jul. 11, 2018. 4 pages (50198EP).
Estrada-Ortiz, Natalia, et al. "Artificial Macrocycles as Potent p53-MDM2 Inhibitors," ACS Med. Chem. Lett. 2017, 8, 1025-1030, 6 pages.
Surmiak, Ewa, et al. "Rational design and synthesis of 1,5-disubstituted tetrazoles as potent inhibitors of the MDM2-p53 interaction," European Journal of Medicinal Chemistry, 126, (2017) 384-407, 24 pages.
Suryakiran, N., et al. "Facile N-tert-butoxycarbonylation of amines using La(NO3)3•6H2O as a mild and efficient catalyst under solvent-free conditions," Tetrahedron Letters, 47 (2006), 8039-8042; 4 pages.
Lin, H., et al. "L-Thyroxine vs. 3,5,3'-triiodo-L-thyronine and cell proliferation: activation of mitogen-activated protein kinase and phosphatidylinositol 3-kinase," Am. J. Physiol Cell Physiol 296 (2009): C980-C991; 12 pages.
Office Action (dated Jul. 21, 2010) for U.S. Appl. No. 12/004,979, filed Dec. 21, 2007.
Office Action (dated Jun. 21, 2011) for U.S. Appl. No. 12/947,389, filed Nov. 16, 2010.
Office Action (dated Apr. 4, 2012) for U.S. Appl. No. 12/947,389, filed Nov. 16, 2010.
Office Action (dated Oct. 17, 2012) for U.S. Appl. No. 12/947,389, filed Nov. 16, 2010.
Office Action (dated Mar. 12, 2014) for U.S. Appl. No. 12/947,389, filed Nov. 16, 2010.
Office Action (dated Sep. 4, 2014) for U.S. Appl. No. 12/947,389, filed Nov. 16, 2010.
Notice of Allowance (dated Nov. 16, 2015) for U.S. Appl. No. 12/947,389, filed Nov. 16, 2010.
Office Action (dated May 23, 2012) for U.S. Appl. No. 12/816,287, filed Jun. 15, 2010.
Office Action (dated Apr. 11, 2013) for U.S. Appl. No. 12/816,287, filed Jun. 15, 2010.
Office Action (dated Oct. 24, 2013) for U.S. Appl. No. 12/816,287, filed Jun. 15, 2010.
Office Action (dated May 8, 2014) for U.S. Appl. No. 12/816,287, filed Jun. 15, 2010.
Notice of Allowance (dated May 12, 2015) for U.S. Appl. No. 12/816,287.
Restriction Requirement (dated May 5, 2016) for U.S. Appl. No. 14/977,776.
Office Action (dated Nov. 4, 2016) for U.S. Appl. No. 14/977,776.
Restriction Requirment (dated Sep. 14, 2012) for U.S. Appl. No. 12/626,068, filed Nov. 25, 2009.
Office Action (dated Jan. 4, 2013) for U.S. Appl. No. 12/626,068, filed Nov. 25, 2009.
Notice of Allowance (dated Apr. 29, 2013) for U.S. Appl. No. 12/626,068, filed Nov. 25, 2009.
Office Action (dated Mar. 16, 2011) for U.S. Appl. No. 11/663,047, filed Oct. 9, 2007.
Notice of Allowance (dated Aug. 22, 2011) for U.S. Appl. No. 11/663,047, filed Oct. 9, 2007.
Office Action (dated Apr. 8, 2013) for U.S. Appl. No. 11/786,723, filed Apr. 11, 2007.
Office Action (dated Oct. 5, 2012) for U.S. Appl. No. 12/644,493, filed Dec. 22, 2009.
Office Action (dated Oct. 16, 2014) for U.S. Appl. No. 12/644,493, filed Dec. 22, 2009.
Office Action (dated Oct. 12, 2016) for U.S. Appl. No. 12/644,493, filed Dec. 22, 2009.
Office Action (dated Apr. 24, 2017) for U.S. Appl. No. 12/644,493, filed Dec. 22, 2009.
Restriction Requirement (dated Oct. 8, 2010) for U.S. Appl. No. 11/992,152, filed Nov. 3, 2009.
Office Action (dated Dec. 10, 2010) for U.S. Appl. No. 11/992,152, filed Nov. 3, 2009.
Office Action (dated Apr. 2, 2013) for U.S. Appl. No. 13/156,047, filed Jun. 8, 2011.
Office Action (dated Feb. 25, 2014) for U.S. Appl. No. 13/156,047, filed Jun. 8, 2011.
Office Action (dated Apr. 16, 2015) for U.S. Appl. No. 13/156,047, filed Jun. 8, 2011.
Notice of Allowance (dated Nov. 2, 2015) for U.S. Appl. No. 13/156,047, filed Jun. 8, 2011.
Restriction Requirement (dated Feb. 7, 2013) for U.S. Appl. No. 13/345,194, filed Jan. 6, 2012.
Office Action (dated Apr. 29, 2013) for U.S. Appl. No. 13/345,194, filed Jan. 6, 2012.
Office Action (dated Oct. 15, 2013) for U.S. Appl. No. 13/345,194, filed Jan. 6, 2012.
Notice of Allowance (dated Feb. 6, 2014) for U.S. Appl. No. 13/345,194, filed Jan. 6, 2012.
Restriction Requirement (dated Mar. 13, 2012) for U.S. Appl. No. 12/751,375, filed Mar. 31, 2010.
Office Action (dated Jul. 13, 2012) for U.S. Appl. No. 12/751,375, filed Mar. 31, 2010.
Office Action (dated Apr. 12, 2013) for U.S. Appl. No. 12/751,375, filed Mar. 31, 2010.
Office Action (dated Jan. 12, 2015) for U.S. Appl. No. 12/751,375, filed Mar. 31, 2010.
Office Action (dated Jun. 3, 2015) for U.S. Appl. No. 12/751,375, filed Mar. 31, 2010.

(56) References Cited

OTHER PUBLICATIONS

Notice of Allowance (dated Jul. 7, 2015) for U.S. Appl. No. 12/751,375, filed Mar. 31, 2010.
Restriction Requirement (dated May 18, 2007) for U.S. Appl. No. 10/943,072, filed Sep. 14, 2004.
Office Action (dated Jul. 9, 2007) for U.S. Appl. No. 10/943,072, filed Sep. 14, 2004.
Office Action (dated Dec. 21, 2007) for U.S. Appl. No. 10/943,072, filed Sep. 14, 2004.
A.D.A.M. Medical Encyclopedia, www.ncbi.nlm.nih.gov/pubmedhealth/PMH0001308/, downloaded Jul. 12, 2012. 6 pages.
Abdollahi et al., "Inhibition of αvβ3 Integrin Survival Signaling Enhances Antiangiogenic and Antitumor Effects of Radiotherapy", Clin. Cancer Research., 11(17):6270-6279 (2005) 10 pages.
Albert et al., "Integrin αvβ3 Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.
Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-α in tumorigenesis: inhibition of cell growth and angiogenic factors", Cell Prolif., 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.
Almog et al., "Transcriptional Switch of Dormant Tumors to Fast-Growing Angiogenic Phenotype", Cancer Res., 69(3):836-844 (2009).
Amirkhosravi et al., "Antimetastatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, Supplemental European Search Report dated Apr. 20, 2015. 7 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Application No. PCT/US2017/36396, International Search Report dated Sep. 1, 2017.
Application No. PCT/US2014/66154, International Search Report dated Jan. 27, 2015. 12 pages.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estrogen-dependent human breast cancers sensitive and resistant to tamoxifen", Proc. Natl, Acad. Sci. USA, 99(4):2211-2215 (2002) 5 pages.
Bergers et al., "Modes of resistance to anti-angiogenic therapy", Nat. Rev. Cancer, 8(8):592-603 (2008) 23 pages.
Bergh et al., "Integrin αvβ3 contains a cell surface receptor site for thyroid hormone that is linked to activation of mitogen-activated protein kinase and induction of angiogenesis", Endocrinology, 146 (7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.
Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol, 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.

(56) References Cited

OTHER PUBLICATIONS

Bornebroek et al., "Potential for imaging cerebral amyloid deposits using 123l-labelled serum amyloid P component and SPET", Cucl. Med. Commun., 17:929-933 (1996) 6 pages.

Bozarth et al., "An improved method for the quantitation of cellular migration: Rose of αvβ3 integrin in endothelial and smooth muscle cell migration", Meth. Cell Sci., 19(3):179-187 (1997) 9 pages.

Brachmann et al., "The SIR2 gene family, conserved from bacteria to humans, functions in silencing, cell cycle progression, and chromosome stability", Genes Dev. 9:2888-2902 (1995) 15 pages.

Braughler et al., "Involvement of Lipid Peroxidation in CNS Injury", J. Neurotrauma, 9(Suppl. 1):S1-S7 (1992) 8 pages.

Breier et al., "The role of vascular endothelial growth factor in blood vessel formation", Trends in Cell Biol., 6:454_456 (1996) 3 pages.

PCT International Search Report & Written Opinion dated Sep. 13, 2022 corresponding to PCT International Application No. PCT/US22/31876.

Mexican Office Action (dated May 11, 2022) for Patent Application No. MX/a/2020/010539—Filing Date Oct. 6, 2020.

Mexican Office Action (dated Aug. 1, 2022) for Patent Application No. MX/a/2020/010539—Filing Date Oct. 6, 2020.

Russian Search Report and Office Action (dated Jul. 25, 2022) for Patent Application No. 2020132052/04—Filing Date Sep. 29, 2020.

PCT International Preliminary Report on Patentability dated Nov. 10, 2022 corresponding to PCT International Application No. PCT/US2021/024294 filed Mar. 26, 2021.

Darwish et al., A Novel Fluorobenzyl Polyethylene Glycol Conjucated Tetraiodothyroacetic Acid (fb-PMT), Targeting Thyrointegrin av(33 in Treatment Acute Myeloid Leukemia, Research Square, Aug. 3, 2021 [retrieved on Mar. 21, 2023]. Retrieved from the Internet: <URL:https://www.researchsquare.com/article/rs-754222/v1>. pp. 1-22.

Godugu et al., Anti-Cancer Activities of Thyrointegrin av(33 Antagonist Mono- and Bis-Triazole Tetraiodothyroacetic Acid Conjugated via Polyethylene Glycols in Glioblastoma, Cancers, vol. 13, No. 2780, Oct. 31, 2022 [retrieved on Mar. 21, 2023]. Retrieved from the Internet: <URL: https://www.mdpi.com/2072-6694/13/11/2780>. pp. 1-14.

JP Office Action (dated Apr. 4, 2023) for Patent Application No. JP2020-555772—filed Oct. 6, 2020.

PCT International Search Report and Written Opinion of International Searching Authority dated Apr. 7, 2023 corresponding to PCT International Application No. PCT/US2022/051900 filed Dec. 6, 2022.

Canadian Office Action (dated May 17, 2023) for Patent Application No. CA3026504—filed Jun. 7, 2017.

\* cited by examiner

POLYMER CONJUGATED THYROINTEGRIN ANTAGONISTS

TECHNICAL FIELD

The present disclosure relates generally to thyroid hormone receptor antagonists (referred to as "thyrointegrin antagonists") compounds along with compositions comprising the same, methods of using such compounds and compositions for treating conditions, and methods of synthesis. More specifically the present disclosure relates to compounds comprising alpha-V-beta-3 ($\alpha v\beta 3$) integrin-thyroid hormone receptor antagonists conjugated to a polymer, wherein the polymer may also be conjugated to a further substituent or functional group. The conjugation between the thyrointegrin antagonist and the polymer may be a direct connection, i.e., may not require an intervening linker or moiety.

BACKGROUND

Integrins are a super-family of cell surface adhesion receptors, which control the attachment of cells with the solid extracellular environment, both to the extracellular matrix (ECM), and to other cells. Adhesion is of fundamental importance to a cell; it provides anchorage, cues for migration, and signals for growth and differentiation. Integrins are directly involved in numerous normal and pathological conditions, and as such are primary targets for therapeutic intervention. Integrins are integral transmembrane proteins, heterodimers, whose binding specificity depends on which of the 14$\alpha$-chains are combined with which of the 8$\beta$-chains. The integrins are classified in four overlapping subfamilies, containing the $\beta 1$, $\beta 2$, $\beta 3$ or $\alpha v$ chains. A cell may express several different integrins from each subfamily. In the last several decades, it has been shown that integrins are major receptors involved in cell adhesion, and so may be a suitable target for therapeutic intervention. Integrin $\alpha v\beta 3$ regulates cell growth and survival, since ligation of this receptor can, under some circumstances, induce apoptosis in tumor cells. Disruption of cell adhesion with anti-$\alpha v\beta 3$ antibodies, RGD peptides, and other integrin antagonists has been shown to slow tumor growth.

Applicant has previously disclosed compounds and compositions comprising polymer conjugated with $\alpha v\beta 3$ integrin thyroid antagonists as well as related methods, for example in U.S. patent application Ser. No. 10/943,072, now U.S. Pat. No. 7,785,632, U.S. patent application Ser. No. 11/663,047, now U.S. Pat. No. 8,071,134, U.S. patent application Ser. No. 11/786,723, now U.S. Pat. No. 8,668,926, U.S. patent application Ser. No. 14/184,889, now U.S. Pat. No. 9,579,300, U.S. patent application Ser. No. 14/185,010, now U.S. Pat. No. 9,750,709, U.S. patent application Ser. No. 14/242,041, now U.S. Pat. No. 9,498,536, and U.S. patent application Ser. No. 15/357,818, now U.S. Pat. No. 10,130,686, the entire contents of all of which are hereby incorporated by reference.

Applicant has also previously disclosed compounds and compositions comprising polymer conjugated with $\alpha v\beta 3$ integrin thyroid antagonists as well as related methods, for example in U.S. patent application Ser. No. 12/816,287, now U.S. Pat. No. 9,220,788, U.S. patent application Ser. No. 14/242,041, now U.S. Pat. No. 9,498,536, and U.S. patent application Ser. No. 14/977,776, now U.S. Pat. No. 9,839,614, the entire contents of all of which are hereby incorporated by reference.

As discussed in these references, conjugation between the polymer and the $\alpha v\beta 3$ integrin thyroid antagonists was achieved by covalent bonds using, for example, an ester, an anhydride, or a sulfhydryl linkage.

Applicant has also previously disclosed compounds and compositions comprising non-cleavable polymer conjugated with $\alpha v\beta 3$ integrin thyroid antagonists as well as related methods, for example in U.S. patent application Ser. No. 15/616,637, now U.S. Pat. No. 10,201,616 and U.S. patent application Ser. No. 16/223,176, now U.S. Pat. No. 10,695,436, the entire contents of both of which are hereby incorporated by reference.

Further, Applicant has previously disclosed compounds, compositions and methods comprising non-cleavable polymer conjugated with $\alpha v\beta 3$ integrin thyroid antagonists and targets of the norepinephrine transporter or the catecholamine transporter (for example, benzyl guanidine or derivatives) as well as related methods, for example in U.S. patent application Ser. No. 15/950,870, now U.S. Pat. No. 10,328,043, U.S. patent application Ser. No. 16/398,342, now U.S. Pat. No. 11,077,082, and U.S. patent application Ser. No. 17/340,843, the entire contents of all of which are hereby incorporated by reference.

Still further, Applicant has previously disclosed compounds, compositions, and methods comprising non-cleavable polymer conjugated with $\alpha v\beta 3$ integrin thyroid antagonists wherein the polymer is further conjugated with an additional substituent (including, but not limited to, an aryl group, an aromatic group, a benzyl group, a phenyl group, a substituted benzyl group, etc.), for example in U.S. patent application Ser. No. 16/862,076, now U.S. Pat. No. 10,961,204 and U.S. patent application Ser. No. 17/173,561, the entire contents of both of which are hereby incorporated by reference.

As described in these references, the compounds, compositions, and methods described in these previous applications and issued patents used a polymer (for example, polyethylene glycol (PEG)) connected to the $\alpha v\beta 3$ integrin thyroid antagonist using a spacer and a moiety "Y".

The presently disclosed embodiments include a direct connection between the polymer and the $\alpha v\beta 3$ integrin thyroid antagonist, for example, without requiring the various linkages, spacers, and/or "Y" moieties described in the references identified above. A compound or composition such as those described herein comprising an $\alpha v\beta 3$ integrin-thyroid hormone receptor antagonist (thyrointegrin antagonist) directly conjugated to a polymer would be well received in the art, as would the treatment methods using such compounds and/or compositions and methods of synthesizing the same.

SUMMARY

According to one aspect, a compound comprises a thyrointegrin antagonist; a non-biodegradable polymer directly conjugated to the thyrointegrin antagonist; and a substituent A bound to the non-biodegradable polymer.

According to another aspect, a compound comprises a general formula:

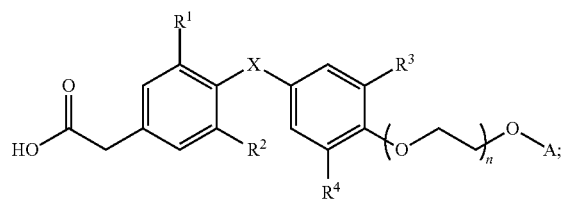

wherein $R^1$, $R^2$, $R^3$ and $R^4$ are each independently selected from the group consisting of hydrogen, iodine, linear alkanes, and branched alkanes; X is oxygen (O) or sulfur (S); n=3-200; and A is selected from the group consisting of: another thyrointegrin antagonist, H, a C1-C10 alkyl optionally substituted with one or more of F, Cl, Br, I, CN, CF3, SO2Me, NO2, CH2N═C(NH2)2, a C4-C7 cycloalkyl optionally substituted with one or more of F, Cl, Br, I, CN, CF3, SO2Me, NO2, CH2N═C(NH2)2, a benzyl group optionally substituted with one or more of F, Cl, Br, I, CN, CF3, SO2Me, NO2, CH2N═C(NH2)2, C1-C5 alkyl, and a phenyl group optionally substituted with one or more of F, Cl, Br, I, CN, CF3, SO2Me, NO2, CH2N═C(NH2)2, C1-C5 alkyl.

According to another aspect, a method of treating comprises providing a compound having a thyrointegrin antagonist, a non-biodegradable polymer directly conjugated to the thyrointegrin antagonist, and a substituent A bound to the non-biodegradable polymer; and administering a therapeutically effective amount of the compound to a patient in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the embodiments will be described in detail with reference made to the following figures, in which like designations denote like members, wherein.

DETAILED DESCRIPTION

Figure 1:
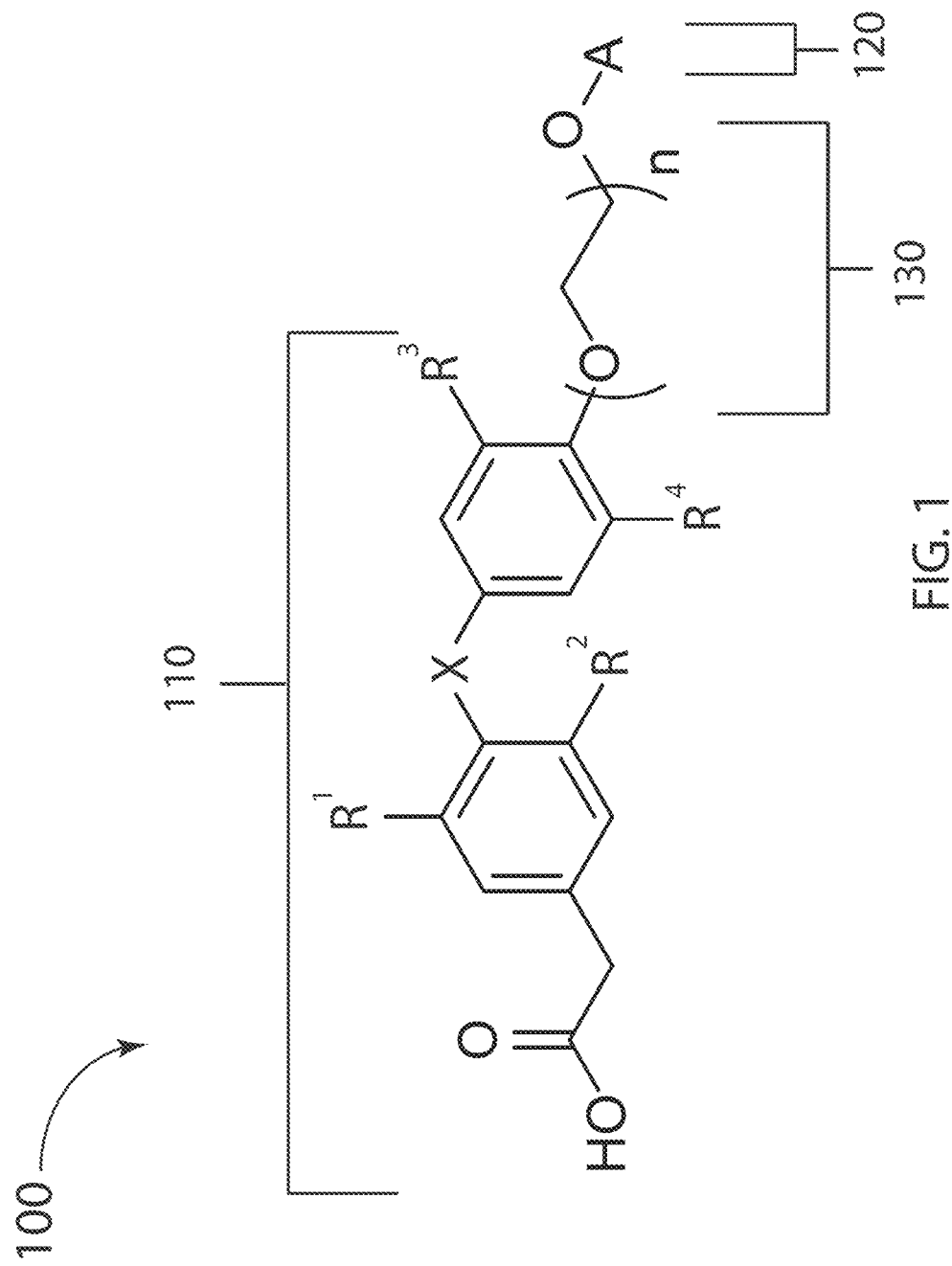
FIG. 1 depicts a general formula of an exemplary compound in accordance with an embodiment of the invention.

A detailed description of the hereinafter-described embodiments of the disclosed composition and method is presented herein by way of exemplification and not limitation with reference to the Figures. Although certain embodiments are shown and described in detail, it should be understood that various changes and modifications might be made without departing from the scope of the appended claims. The scope of the present disclosure will in no way be limited to the number of constituting components, the materials thereof, the shapes thereof, colors thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Overview

Embodiments of the present disclosure describe new chemical compounds, compositions comprising the new chemical compounds, methods of synthesis thereof, and methods of treatment using such compounds and compositions. The compositions described herein may include an anti-angiogenic thyroid hormone or derivative thereof conjugated to a polymer, forming a single chemical entity.

Embodiments of the compositions disclosed herein may be synthesized to include, but are not limited to entities comprising non-biodegradable polymers such as polyethylene glycol (PEG) (100-15,000 Daltons, for example between 1,000-1,600 Daltons), α, β, or γcyclodextrins, chitosan, alginic acid or hyaluronic acid, to a thyrointegrin antagonist. Embodiments of the thyrointegrin antagonists conjugated to the polymers may include tetraiodothyroacetic acid (tetrac), triiodothyroacetic acid (triac), derivatives thereof and variations thereof.

Embodiments of the compositions described herein have been further synthesized and characterized as thyrointegrin antagonists conjugated to different molecular weights of polyethylene glycol (100 to 15,000 Dalton). Additional polymer conjugation were synthesized using bi-functional PEG. Additionally, tetra-function PEG as well as other branched PEG up to 8 chains may be used in embodiments.

Embodiments of each of the compounds described in the current application may have multiple types of utility for treating a plurality of different diseases modulated by angiogenesis or the inhibition thereof. Each of the compositions described in the present disclosure, in view of presence of the thyrointegrin antagonists present in the described compositions, may each have an affinity for targeting the integrin receptor $\alpha v \beta 3$ located on numerous types of cells found throughout the human body and various animal bodies.

For example, the utility of the compositions disclosed herein may be useful for treating angiogenesis-mediated disorders such as cancer (solid tumors and liquid tumors) in humans or mammals. Cancers may include glioblastoma, pancreatic, skin, ovarian, breast, prostate, bladder, lung, and liver cancer. Liquid tumors may also acute myeloid leukemia, multiple myeloma, Lymphoma, and chronic lymphocytic leukemia. The compositions described herein may further treat ocular disorders (diabetic retinopathy and age-related macular degeneration), inflammatory disorders (arthritis, osteoarthritis), atherosclerosis lesions, and dermatology (rosacea, psoriasis, skin cancer) which may each be mediated or dependent upon the generation of new blood cells via angiogenesis to persist and the treatment thereof may be dependent antagonizing the formation of new blood vessel to slow or eliminate the angiogenic pathways.

While embodiments and examples of the present disclosure described herein, for purposes of illustration, modifications and changes will become apparent to those skilled in the art based on the examples illustrated. Accordingly, the appended examples intended to encompass all variations and such modifications and changes that fall within the true spirit and scope of this disclosure.

Reference may be made herein to specific thyrointegrin compounds, for example, tetrac, triac, etc. These phrases include derivatives of such compounds in accordance with the full teachings of this disclosure, even where such derivatives are not specifically listed.

Exemplary Compounds/Compositions

Exemplary compounds will now be described. It will be understood that embodiments of the invention may include compositions comprising such compounds as well as methods of synthesizing such compounds. Further, the disclosed compounds are not intended to limit the scope of embodiments of the invention and many different compounds may be used as is discussed in more detail.

Referring to the drawings, FIG. 1 depicts an embodiment of a general formula 100 comprising a thyrointegrin antagonist 110 conjugated to a polymer 130. The polymer is also conjugated to a substituent 120 (depicted generally as "A"). Hereinafter, the substituent may be referred to as substituent A, substituent 120, or as substituent A 120. FIG. 1 depicts a carboxylic acid form of the general formula 100, as may other figures present in this application. As would be apparent to one skilled in the art, a salt (e.g. a sodium salt) of the general formula 100 may also be used.

The polymer 130 may comprise a polyether such as polyethylene glycol (PEG). Other polymers may be used, including chitosan, alginic acid, hyaluronic acid, and other polymers. In embodiments using PEG as the polymer 130, the polymer may have a molecular weight between 200 and 4,000 g per mole. For example, as shown in FIG. 1, the PEG polymer 130 may comprises n subunits. The number n may be, for example, 3-200. In several non-limiting embodiments, n=36 has been chosen for exemplary purposes. In other non-limiting examples, n=3 or n=16 have been chosen for exemplary purposes. Again, n may be any number, for example, 3-200 in certain embodiments.

The term thyrointegrin antagonist describes a compound that has the ability to inhibit or antagonize one or more thyroid hormone receptors known by a person skilled in the art, for example the integrin family of thyroid hormone receptors, such as the thyroid hormone cell surface receptor $\alpha v \beta 3$. The thyrointegrin antagonist 110 may be an anti-angiogenic thyroid hormone or a thyroid hormone receptor antagonist. For example, the thyrointegrin antagonist 110 may be an alpha-V-beta-3 ($\alpha v \beta 3$) integrin-thyroid hormone receptor antagonist.

Specific embodiments of the thyrointegrin antagonist 110 may include tetraiodothyroacetic acid (tetrac), triiodothyroacetic acid (triac), derivatives thereof and variations thereof. Thyrointegrin antagonists may be of the types described in the above-listed patents and applications incorporated by reference. For example, described in those documents, in some embodiments of the thyrointegrin antagonist 110, the variables depicted as R1, R2, R3, and R4 may each independently be substituted for molecules such as hydrogen, iodine, and alkanes. In some embodiments, the alkanes have four or fewer carbons. In some embodiments, the variable "X" may be defined as an oxygen atom (O) or a sulfur atom (S).

As shown in FIG. 1, the thyrointegrin antagonist 110 may be directly conjugated to the polymer 130. Directly conjugated may mean that there is no linker, spacer, or "Y" moiety as disclosed in the applications incorporated by reference above. For example, as shown in FIG. 1, the thyrointegrin antagonist may be connected to an extended PEG chain via hydrogen bonding without the need for an aliphatic, aromatic, heterocyclic amine or multivalent nitrogen site.

In embodiments of the invention, the substituent A 120 may be selected from the group consisting of: another thyrointegrin antagonist, H, a C1-C10 alkyl optionally substituted with one or more of F, Cl, Br, I, CN, CF3, SO2Me, NO2, CH2N=C(NH2)2, a C4-C7 cycloalkyl optionally substituted with one or more of F, Cl, Br, I, CN, CF3, SO2Me, NO2, CH2N=C(NH2)2, a benzyl group optionally substituted with one or more of F, Cl, Br, I, CN, CF3, SO2Me, NO2, CH2N=C(NH2)2, C1-C5 alkyl, and a phenyl group optionally substituted with one or more of F, Cl, Br, I, CN, CF3, SO2Me, NO2, CH2N=C(NH2)2, C1-C5 alkyl. In embodiments, substituent A may include targets of the norepinephrine transporter or the catecholamine transporter (for example, benzyl guanidine or derivatives) as described, for example in U.S. patent application Ser. No. 15/950,870, now U.S. Pat. No. 10,328,043, U.S. patent application Ser. No. 16/398,342, now U.S. Pat. No. 11,077, 082, and U.S. patent application Ser. No. 17/340,843, incorporated by reference above. Still further, in embodiments, substituent A may include, an aryl group, an aromatic group, a benzyl group, a phenyl group, a substituted benzyl group, etc., as described, for example, in U.S. patent application Ser. No. 16/862,076, now U.S. Pat. No. 10,961,204 and U.S. patent application Ser. No. 17/173,561, incorporated by reference above. In further embodiments, as taught in these references, the substituent A may include a heterobenzyl group, 5 membered ring heteroaryls, fused heteroaryls, qinolines, indoles, heteroarylmethyls, esters, and amides. Still further, in embodiments, when substituent A is an aromatic ring, the aromatic ring may be substituted at one or more locations. In some embodiments of the substituent A 120 comprising the aromatic ring, locations on the aromatic ring may be each independently be substituted for molecules such as hydrogen, iodine, fluorine, bromine, a methoxy group, a nitro group, an amine group, and a nitrile group as described in Table 2 of U.S. patent application Ser. No. 15/950,870 now U.S. Pat. No. 10,328,043 and U.S. patent application Ser. No. 16/398,342 now U.S. Pat. No. 11,077, 082. Still further, the locations may be substituted with alkyls, aryls, halos, amides, and the like.

Figure 2:
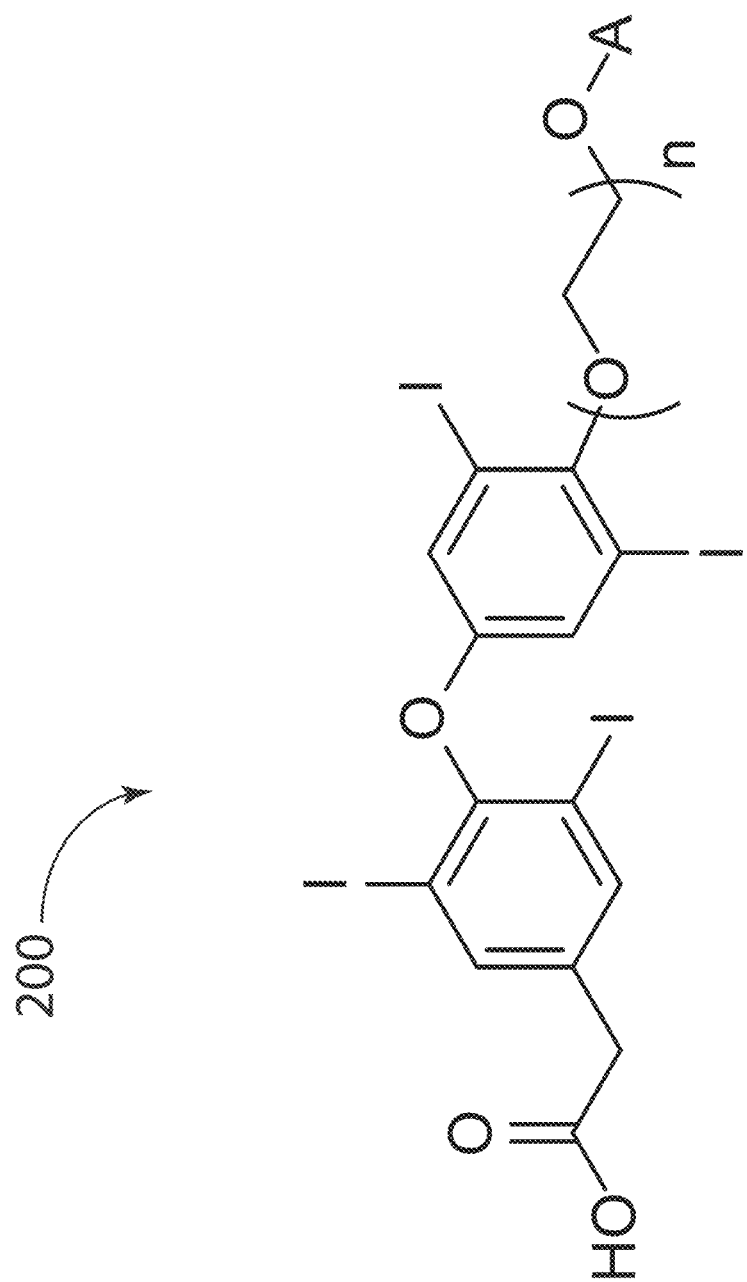
FIG. 2 depicts a further detailed general formula of an exemplary compound in accordance with an embodiment of the invention.

Referring now to FIG. 2, a more detailed general formula 200 is shown. As shown, the variable X is oxygen and all of R1, R2, R3, and R4 are substituted for iodine-thus, the thyrointegrin antagonist is tetraiodothyroacetic acid (tetrac). Substituent A has not been further defined in this figure. The general formula 200 may thus be referred to as P-mono-TET conjugated to substituent A or A-P-mono-TET wherein A refers to the substituent, P-mono refers to polymer/PEG and TET refers to tetraiodothyroacetic acid (tetrac).

Figure 3:
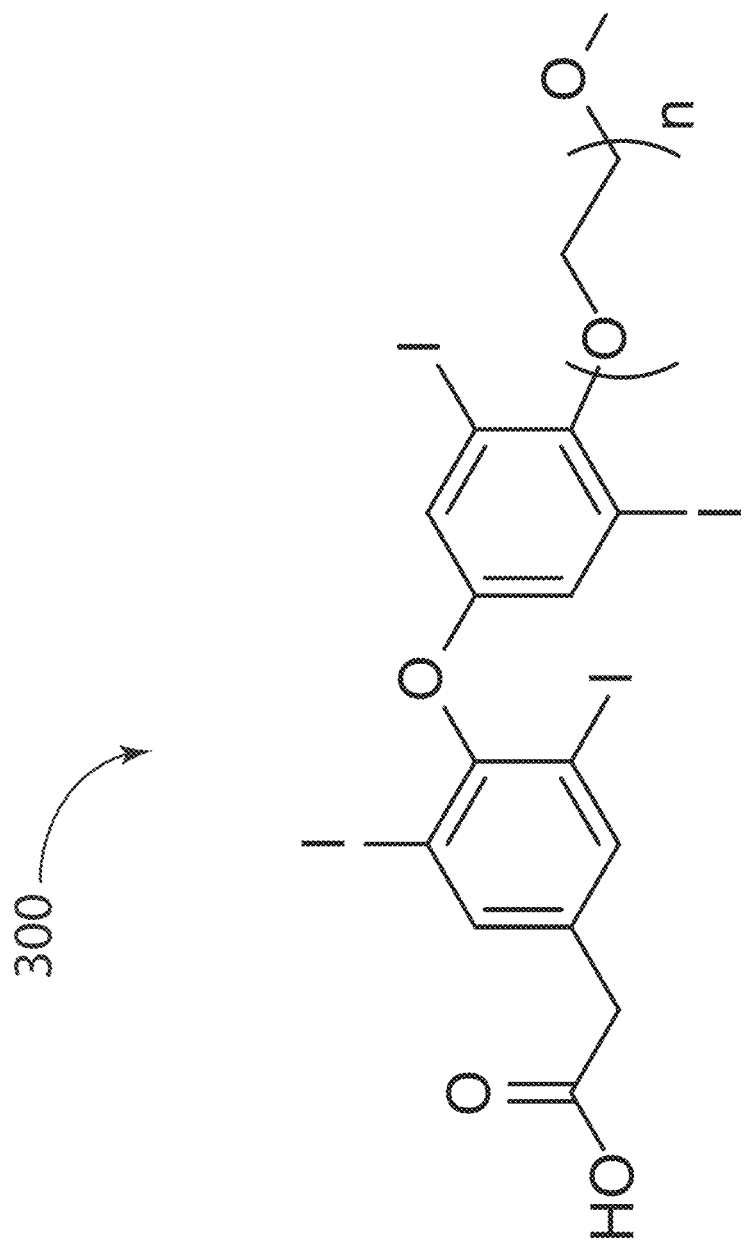
FIG. 3 depicts a further detailed general formula of an exemplary compound in accordance with an embodiment of the invention.

Referring now to FIG. 3, an even more detailed formula 300 is shown. General formula 300 includes the P-mono-TET structure of FIG. 2 (X is oxygen and all of R1, R2, R3, and R4 are iodine) and A is a methyl group. For convenience, this structure 300 is referred to as m-P-mono-TET with m referring to methyl, P-mono referring to polymer/PEG, and TET referring to tetraiodothyroacetic acid (tetrac).

Figure 4:
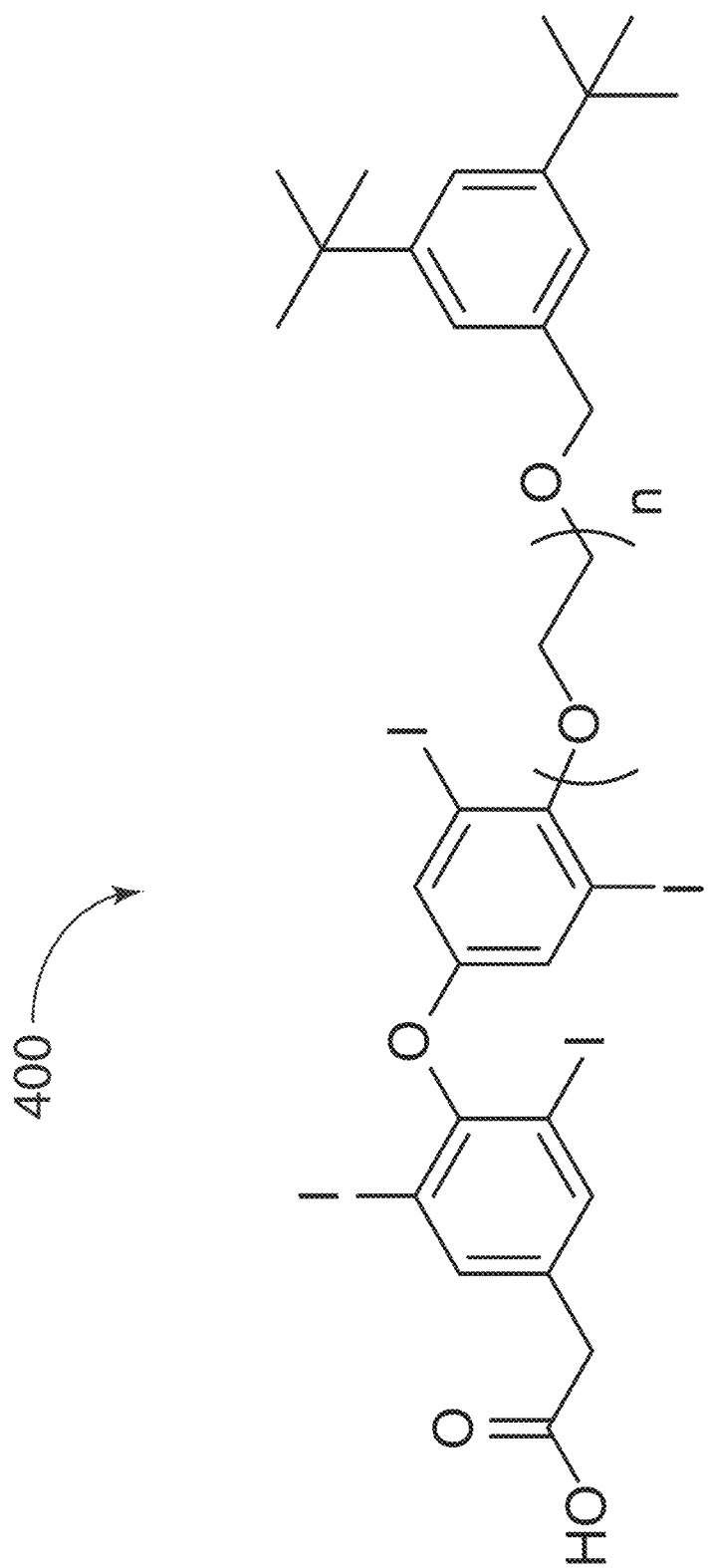
FIG. 4 depicts a further detailed general formula of an exemplary compound in accordance with an embodiment of the invention.

Referring now to FIG. 4, another more detailed formula is shown, namely general formula 400. General formula 400 includes the P-mono-TET structure of FIGS. 2 and 3 (X is oxygen and all of R1, R2, R3, and R4 are iodine) while A is a substituted benzyl. While the benzyl group is substituted at two positions in the depicted embodiment, it will be understood that additional or alternative substitutions may be included, for example, at additional or alternative positions. For convenience, this structure 400 is referred to as di-tbutylbenzyl conjugated to tetrac by PEG, or dtbb-P-mono-TET.

Figure 5:
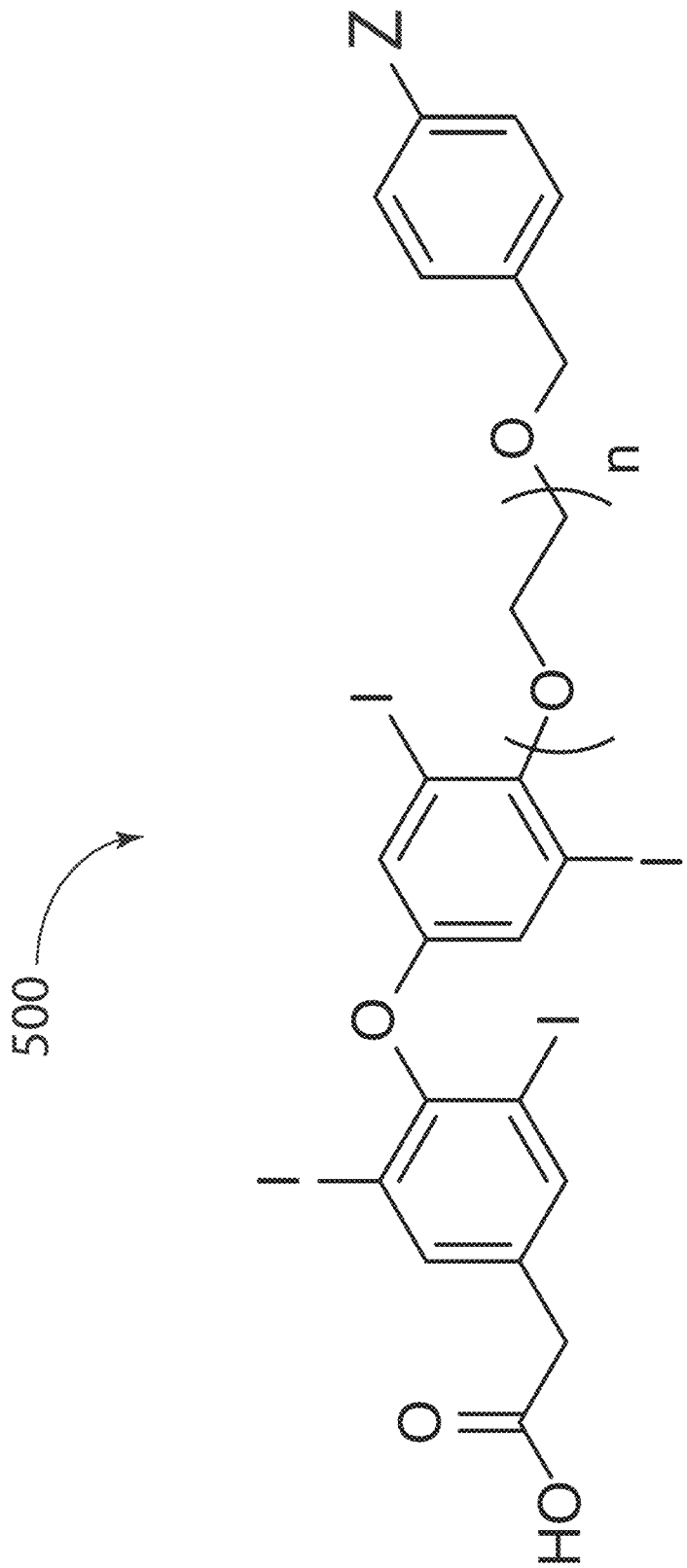
FIG. 5 depicts a further detailed general formula of an exemplary compound in accordance with an embodiment of the invention.

Referring now to FIG. 5, another more detailed formula is shown, namely formula 500. General formula 500 includes the P-mono-TET structure of FIG. 2-4 (X is oxygen and all of R1, R2, R3, and R4 are iodine) while A is again a substituted benzyl, wherein the benzyl group is substituted with a variable "Z". In embodiments, Z may be a halogen. Again, while the benzyl group is substituted at only one position in the depicted embodiment, it will be understood that additional or alternative substitutions may be included, for example, at additional or alternative positions.

Figure 6:
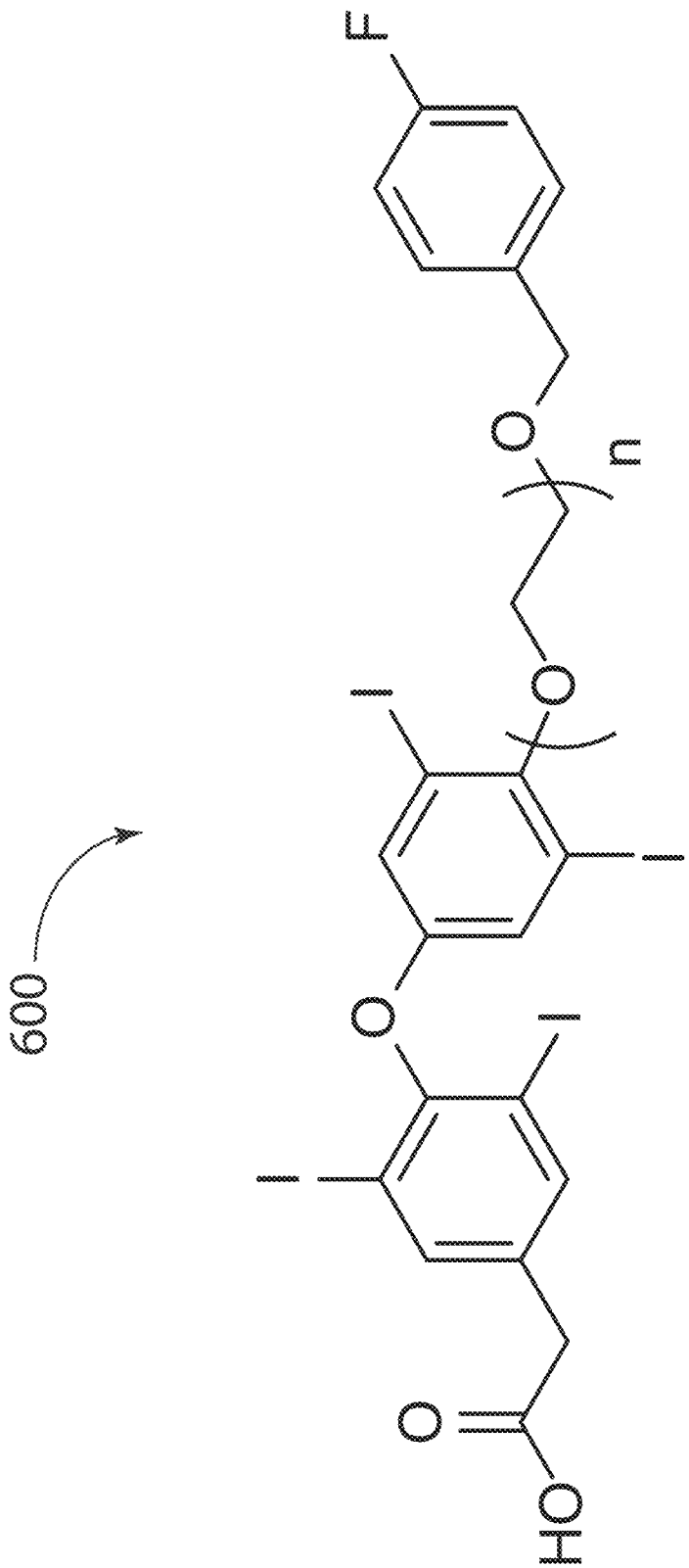
FIG. 6 depicts a further detailed general formula of an exemplary compound in accordance with an embodiment of the invention.

Referring now to FIG. 6, another more detailed formula is shown, namely formula 600. General formula 600 includes the P-mono-TET structure of FIG. 2-5 (X is oxygen and all of R1, R2, R3, and R4 are iodine) while A is a substituted benzyl group as discussed above with respect to FIG. 5. Further, in FIG. 6, the benzyl group is substituted with fluoride; thus, the substituent A is fluorobenzyl. For convenience, this structure 500 is referred to as fluorobenzyl-P-mono-TET or fb-P-mono-TET.

In still further embodiments, the compositions/polymer described throughout this disclosure may be multi-functional, for example, bi-functional or tetra-functional compositions, for example, as taught in U.S. patent application Ser. No. 15/616,637, now U.S. Pat. No. 10,201,616 and U.S. patent application Ser. No. 16/223,176, now U.S. Pat. No. 10,695,436, incorporated by reference above. The term "bi-functional" may refer to a compound having two thyroid antagonists or derivatives thereof conjugated to the same polymer 130. The term "tetra-functional" may refer to a compound having four thyroid antagonists or derivatives thereof conjugated to the same polymer 130.

Figure 7:
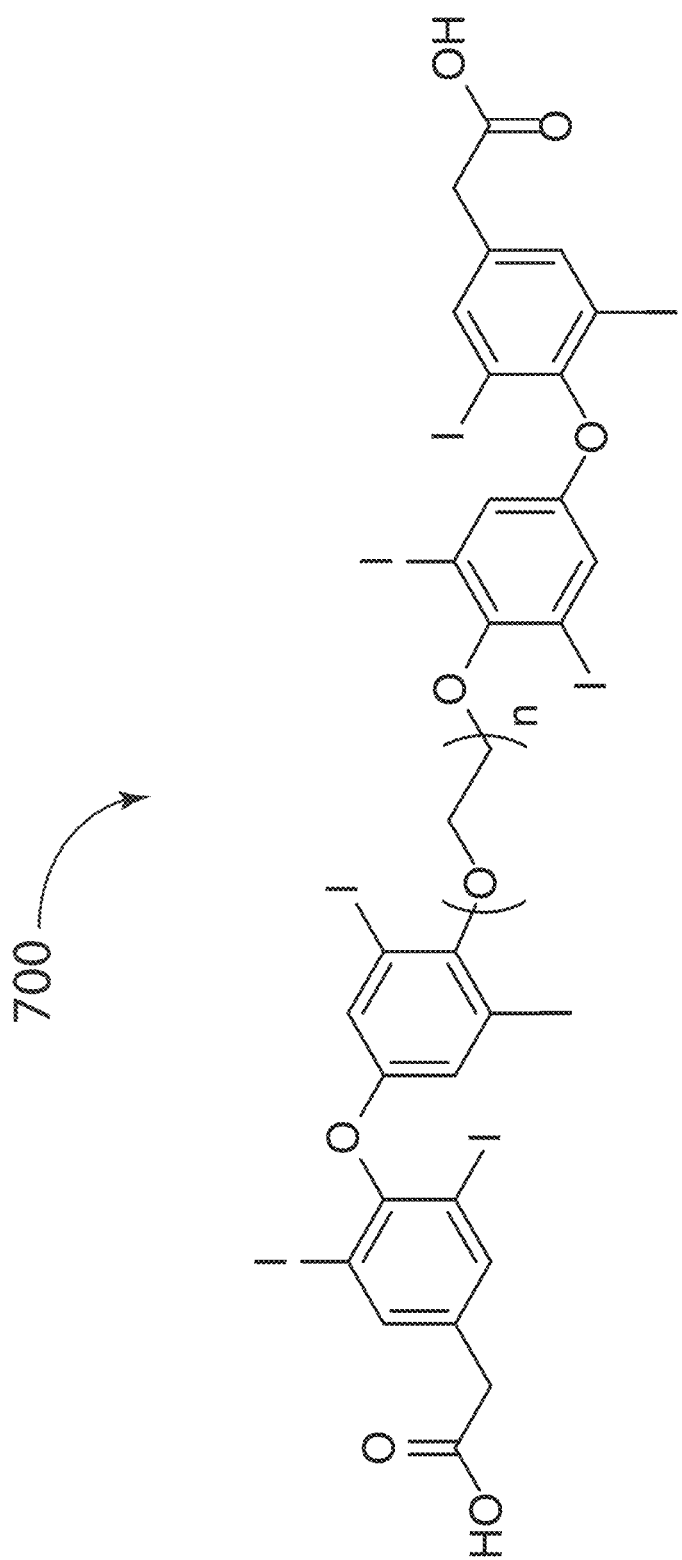
FIG. 7 depicts a further detailed general formula of an exemplary compound in accordance with an embodiment of the invention.

An example of a bifunctional composition can be seen in FIG. 7 showing another more detailed formula is shown, namely formula 700. General formula 700 includes the polymer and tetrac structure of FIG. 2-6 (X is oxygen and all of R1, R2, R3, and R4 are iodine) while A is another thyrointegrin antagonist, namely, tetrac. This formula may alternatively be conceived of as not having a substituent A, but instead having a second thyrointegrin antagonist also directly conjugated to the polymer. General formula 700 may be referred to as P-bi-TET, wherein P refers to polymer/PEG, TET refers to tetraiodothyroacetic acid (tetrac), and bi refers to the bifunctional nature of the polymer and/or the presence of two tetrac moieties.

As discussed above, the composition/polymer may also be tetra-functional and may have four thyrointegrin antagonists conjugated to a single polymer. Other variations may also be used in embodiments.

Further, while the specific embodiments shown in FIGS. 2-7 include tetrac (tetraiodothyroacetic acid), in other embodiments triac (triiodothyroacetic acid), derivatives of tetrac or triac, and/or combinations thereof may be used.

EXEMPLARY SYNTHESIS

Synthesis of some of the specific exemplary compounds described herein are demonstrated below. These synthesis descriptions are provided only as examples and are not intended to limit the disclosure.

Example 1: Synthesis of m-P-Mono-TET

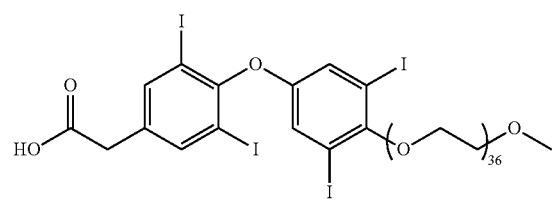

Figure 8:
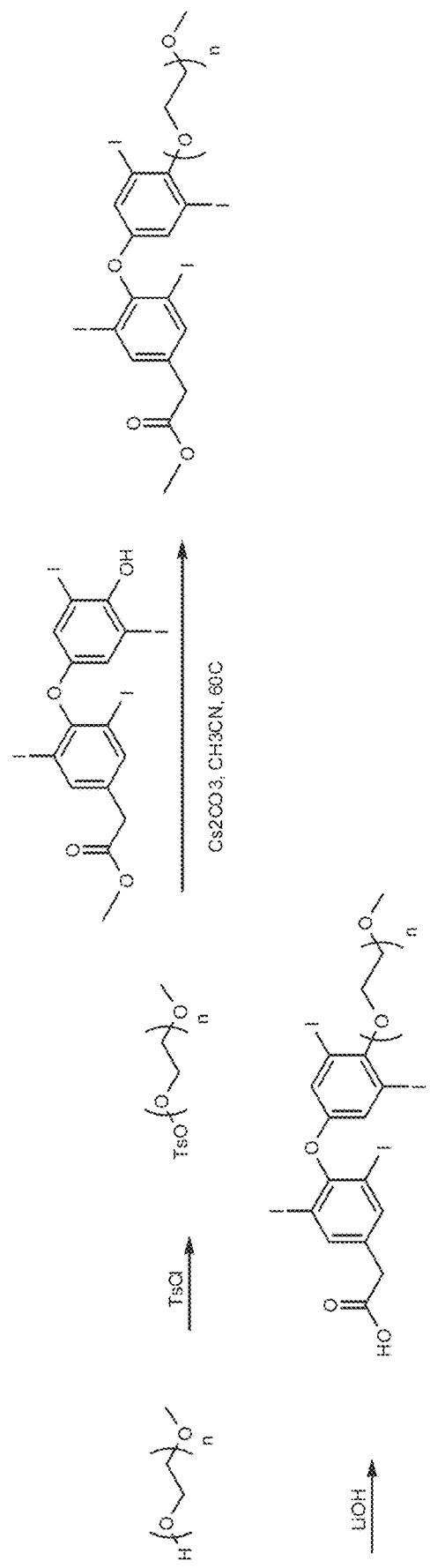
FIG. 8 depicts an exemplary synthetic pathway of an exemplary compound in accordance with an embodiment of the invention.

FIG. 8 depicts an overview of a synthetic pathway for P-Mono-TET. While n may be any number within the range disclosed in this application as shown in the Figure, in one embodiment, n may be equal to 36 as shown in the above formula. In other embodiments, n may be equal to 16 or may be equal to 3. The individual steps of the scheme of synthesis of m-P-mono-TET will be described in more detail below:

Step 1: mPEGnOH (1 eq) was dissolved at 5% w/v in DCM, followed by tosyl chloride (3 eq), and triethylamine (3 eq). The reaction was kept stirring for 24 h at room temperature. After removing of solvent, the tosylated product mPEGn-OTs was separated by silica gel chromatography using DCM/Methanol as mobile phase. mPEG36Tos yield=80%. HPLC>95% pure, tR=18.17 min MS (ESI+) calcd 1772 found 1772.5.

Step 2: 1.2 equivalent of Tetrac methyl ester (Bioconjugate Chemistry (2019), 30(12), 3087) was dissolved at 5% w/v in anhydrous acetonitrile, Cs2CO3 (2 eq) was added, and the reaction was stirred at room temperature for 30 min. 1 equivalent of the PEG tosylate from the previous step was then added, and the mixture was refluxed for 24 h. After cooling, the reaction mixture was filtered to remove Cs2CO3. Solvents were removed under reduced pressure, and the oily residue was purified via silica gel chromatography using DCM:MeOH as eluent.

Step 3: A 27 mM suspension of the methyl ester product from the previous step was stirred with 5 eq of LiOH in THF:water (2:1) for 2 h. The lithium salt of acid was neutralized by diluted HCl, the THF was removed under reduced pressure, the product was extracted with DCM, the combined organic layers were dried and the solvent removed to recover the final product. Purity was >95% (HPLC), tR=30.47 min. MS (ESI+) calcd 2347 found 2347.1.

Similar procedures were followed for embodiment in which n=16 with the following results: HPLC purity >95%, tR=30.13 min. MS (ESI+)=1489.7 (M+Na). Likewise, similar procedures were followed for embodiment in which n=3 with the following results: HPLC>95% pure, tR=29.97 min. MS (ESI+) calcd 894 found 894.1.

Example 2: Synthesis of P-bi-TET

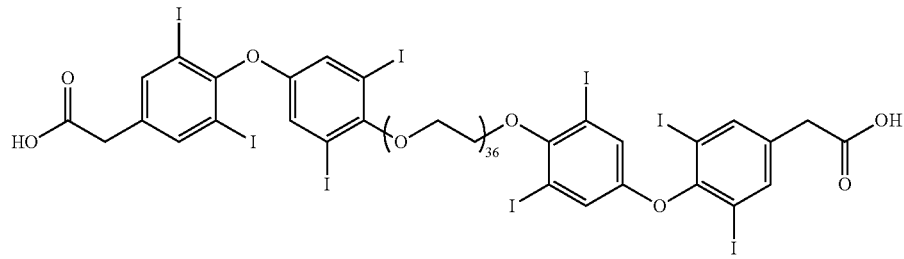

Figure 9:
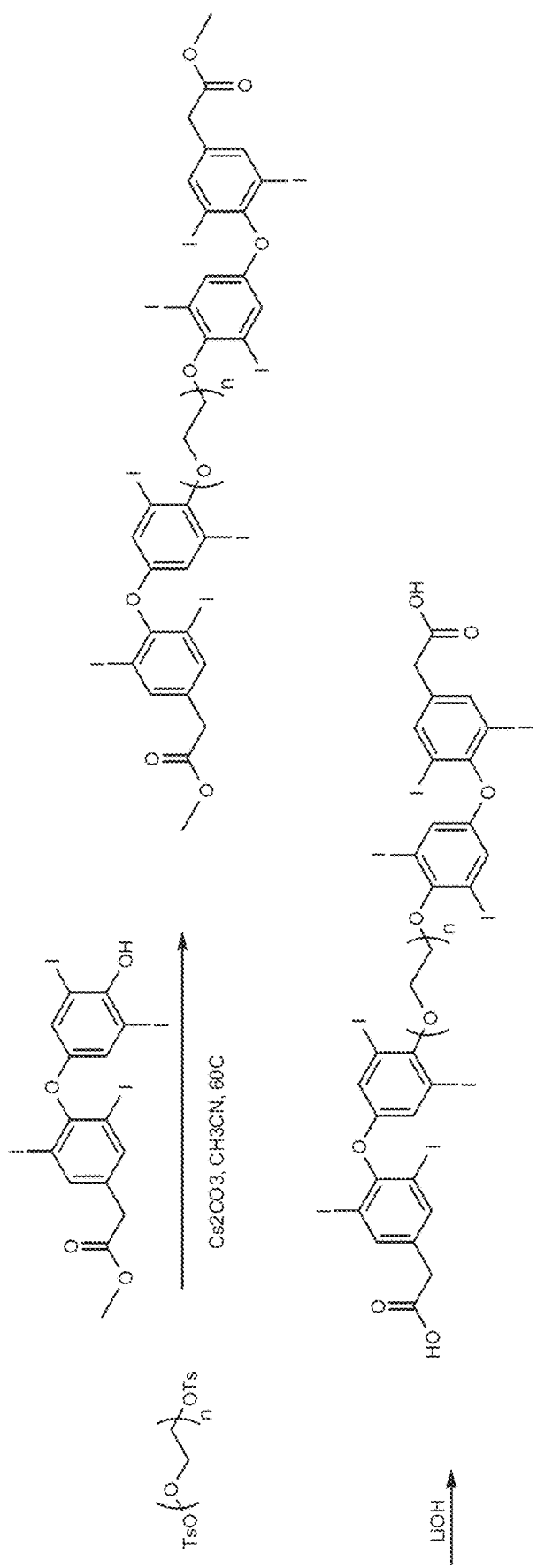
FIG. 9 depicts an exemplary synthetic pathway of an exemplary compound in accordance with an embodiment of the invention.

FIG. 9 depicts an overview of a synthetic pathway for P-bi-TET (for example with n=36 as shown). The individual steps of the scheme of synthesis of P-bi-TET will be described in more detail below:

Step 1: 119 mg (3 eq) of tetrac methyl ester (Bioconjugate Chemistry 2019, 30, 3087) and 51 mg (3 eq.) Cs2CO3 were stirred for 20 minutes in 6 ml of anhydrous acetonitrile. Then 100 mg (1 eq) of PEG36 bis tosylate (Journal of Medicinal Chemistry 2021, 64, 6300) was added, and the reaction was stirred at 60 C for 18 h under nitrogen, at which time HPLC analysis indicated that the reaction was complete. The reaction was cooled, the acetonitrile was removed under reduced pressure, and the residue was partitioned between dichloromethane and saturated brine. The layers were separated, the aqueous layer was extracted three times with DCM, and the solvent was removed from the combined DCM layers under reduced pressure. The residue was chromatographed on silica gel using 0-20% methanol in dichloromethane, yielding 61 mg of product, 38% yield. HPLC retention time 41.437 minutes.

Step 2: The product from the previous step was dissolved in 750 uL of THF, and 15 mg of lithium hydroxide in 750 uL of water was added. The reaction was stirred overnight, at which point HPLC analysis indicated that the reaction was complete. The mixture was acidified to pH 2 with a few drops of dilute HCl, the THF was removed under reduced pressure, and the residue was partitioned between dichloromethane and brine. The layers were separated, the aqueous layer was extracted three times with dichloromethane, the solvent was removed from the combined organic layers, and the residue was chromatographed on silica gel in 0-20% methanol/DCM with 0.5% formic acid. 18 mg (18%) of final product was obtained. HPLC retention time 39.788 minutes, m/z 1532.5 ([M+2H]).

Example 3: Synthesis of Dtbb-P-Mono-TET

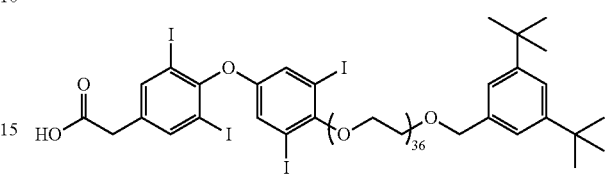

Figure 10:
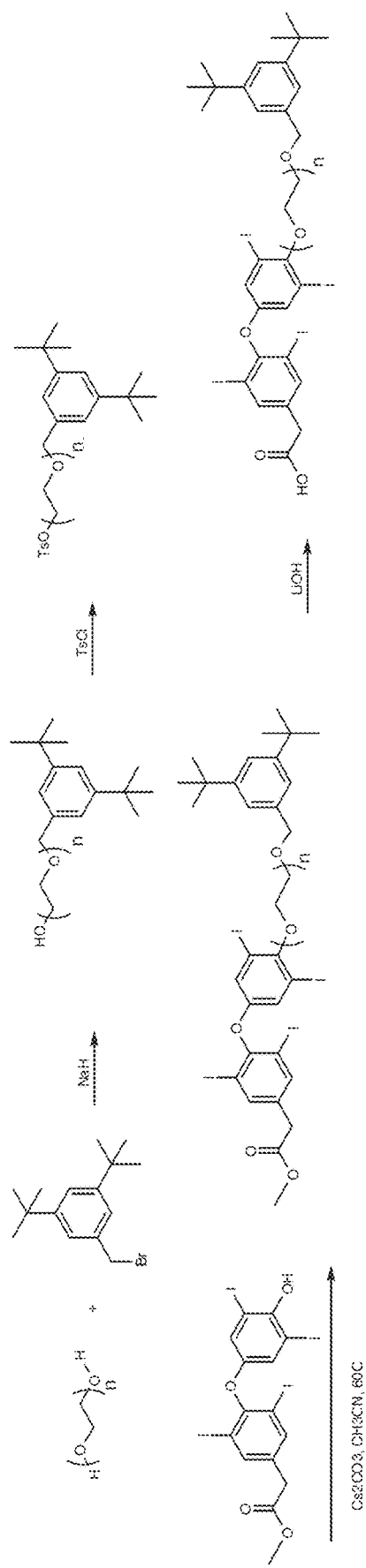
FIG. 10 depicts an exemplary synthetic pathway of an exemplary compound in accordance with an embodiment of the invention.

FIG. 10 depicts an overview of a synthetic pathway for Dtbb-P-Mono-TET (for example, with n=36 as shown). The individual steps of the scheme of synthesis of Dtbb-P-Mono-TET will be described in more detail below:

Step 1: A round bottom flask was charged with 15 mg (3 eq.) of 60% Sodium hydride in 10 ml of anhydrous THF, under nitrogen atmosphere. 200 mg (0.124 mmol) of bis hydroxypolyethylene glycol 36 was added, the reaction was stirred for 15 minutes, then 35 mg (1 eq) of 3,5-ditertbutyl-benzylbromide was added. The reaction was stirred overnight, quenched with saturated sodium bicarbonate solution, and the THF was removed under reduced pressure. The residue was partitioned between dichloromethane and saturated brine, the layers were separated, the aqueous layer was extracted 3 times more with dichloromethane, the solvent was removed from the combined organic layers, and the residue was chromatographed on silica gel with 0-20% methanol in dichloromethane. The bisbenzyl bi-product came out first, followed by the desired product, mono-3,5-ditertbutylbenzyl PEG36-OH. 80 mg, 0.0446 mmol, 36% yield.

Step 2: The product from the last step along with 3 equivalents of triethylamine was dissolved in 10 ml of dichloromethane, then 2 equivalents of Tosyl chloride was added portionwise. The reaction was stirred overnight, washed with saturated brine, the solvents were removed under reduced pressure, and the residue was chromatographed on silica gel in 0-10% methanol in dichloromethane, yielding 70 mg (80%) of the monotosylated PEG product.

Step 3: 29 mg (1.5 eq) of tetrac methyl ester (Bioconjugate Chemistry (2019), 30(12), 3087) and 16.6 mg (2 eq.) Cs2CO3 were stirred for 20 minutes in 2 ml of anhydrous acetonitrile. Then 50 mg (1 eq) of the product from the previous step was added, and the reaction was stirred at 60

C for 18 h under nitrogen, at which time HPLC analysis indicated that the reaction was complete. The reaction was cooled, the acetonitrile was removed under reduced pressure, and the residue was partitioned between dichloromethane and saturated brine. The layers were separated, the aqueous layer was extracted three times with DCM, and the solvent was removed from the combined DCM layers under reduced pressure. The residue was chromatographed on silica gel using 0-10% methanol in dichloromethane, yielding 34 mg of product, 52% yield. HPLC retention time 42.726 minutes, m/z 1276.3 ([M+2H]).

Step 4: The product from the previous step was dissolved in 250 uL of THF, and 5 mg of lithium hydroxide in 250 uL of water was added. The reaction was stirred overnight, at which point HPLC analysis indicated that the reaction was complete. The mixture was acidified to pH 2 with a few drops of dilute HCl, the THF was removed under reduced pressure, and the residue was partitioned between dichloromethane and brine. The layers were separated, the aqueous layer was extracted three times with dichloromethane, the solvent was removed from combined organic layers, and the residue was chromatographed on silica gel in 0-20% methanol/DCM with 0.5% formic acid. 13 mg (40%) of final product was obtained. HPLC retention time 42.219 minutes, m/z 1269 ([M+2H]).

Again, other synthetic pathways in addition to those described above may be used to produce the exemplary compounds. Further, additional compounds may be generated using the techniques described above, modified as needed for the respective substitutions. For example, in embodiments, triiodothyroacetic acid (triac) may be used instead of tetrac. Likewise, derivatives of tetra and/or triac may be used.

Binding Affinity

Figure 11A:
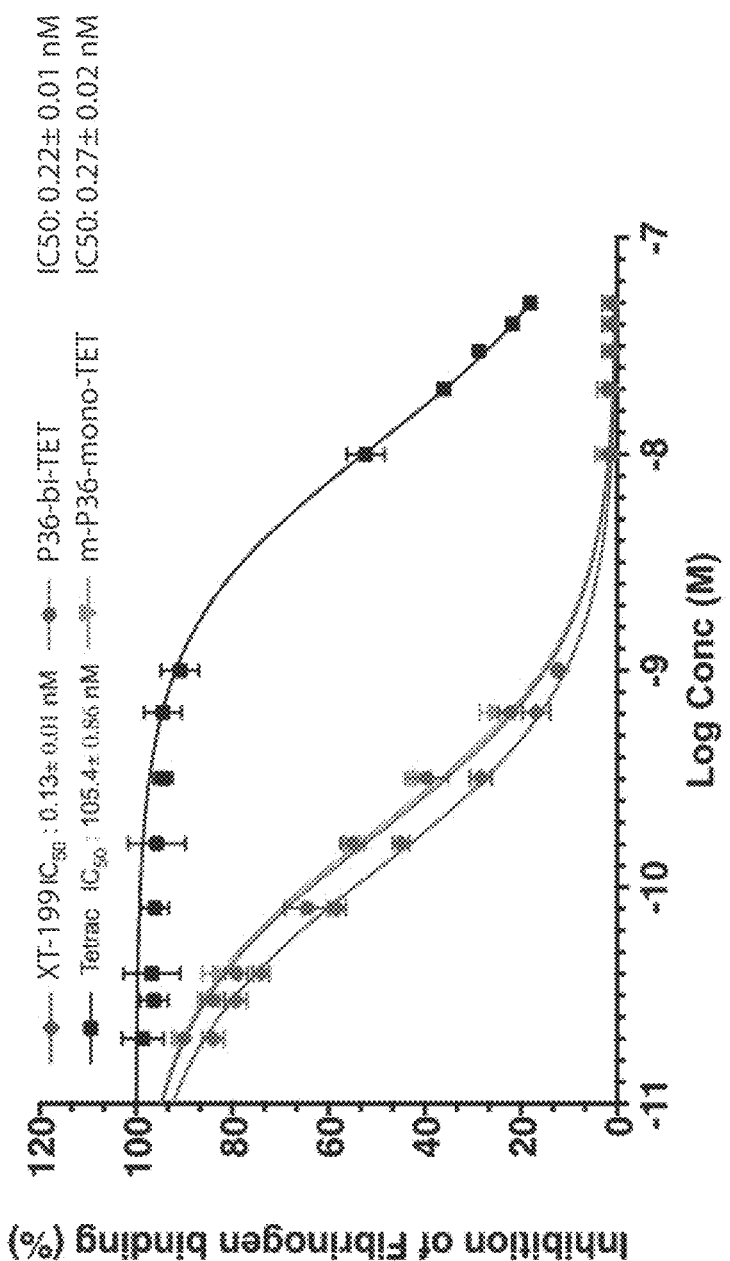
FIG. 11A depicts binding affinity of exemplary compounds and reference compounds in accordance with an embodiment of the invention.

The binding affinity of exemplary compounds is show in FIG. 11A, including P-bi-TET and m-P-mono-TET (both having n=36). The method was as follows: The binding affinity of P-bi-TET and m-P-mono-TET to purified αvβ3 was measured using the method described by Li, W., et al., *Pharmacokinetics, Biodistribution, and Anti-Angiogenesis Efficacy of Diamino Propane Tetraiodothyroacetic Acid-conjugated Biodegradable Polymeric Nanoparticle.* Sci Rep, 2019. 9(1): p. 9006. Ninety-six polystyrene microtiter plates coated with fibrinogen and incubated at 4° C. overnight. The wells were blocked with 3% BSA for 2 hours at room temperature and were washed with buffer A (50 mM Tris/HCl, 100 mM NaCl, 1 mM $CaCl_2$), 1 mM $MgCl_2$, 1% BSA) for three times. Integrins αvβ3 and increasing concentrations of P-bi-TET or m-P-mono-TET were added and incubated for 2 hours at room temperature, and then wells were washed three times with buffer A and incubated with a streptavidin HRP conjugate (1:1000 in buffer A) for 1 hour at room temperature. Finally, wells were washed three times with buffer A and 100 μL peroxidase substrate TMB was added, and the reaction was terminated after 30 minutes with 50 μL of 450 nm stop solution for TMB. Absorbance was determined at 450 nm with a Microplate Reader (Bio-Rad, Hercules, Calif., USA). The best-fit 50% inhibitory concentration ($IC_{50}$ value) for the compounds were calculated by fitting the data with nonlinear regression using GraphPad Prism (GraphPad, San Diego, Calif.).

FIG. 11A shows binding affinity for test compounds P-bi-TET (n=36) and m-P-mono-TET (n=36) relative to controls XT199 and tetrac. XT199 is a standard high affinity small molecule non-peptide with acidic (carboxylic acid terminal) and basic (guanidine terminal) moieties separated by approximately 14 Angstrom for docking into the cationic and anionic binding domain of αvβ3 binding sites and has a binging affinity of 0.13±0.01 nM. Tetrac (unconjugated) has a lower αvβ3 affinity binding of 105.4±0.86 nM as shown in the Figure. However, as shown, the test compounds P-bi-TET and m-P-mono-TET (n=36) show much higher affinity binding than tetrac, for example, 0.22±0.01 nM and 0.27±0.02 nM, respectively. Thus, the disclosed compounds demonstrate improved binding affinity for αvβ3 when compared with unconjugated tetrac.

Figure 11B:
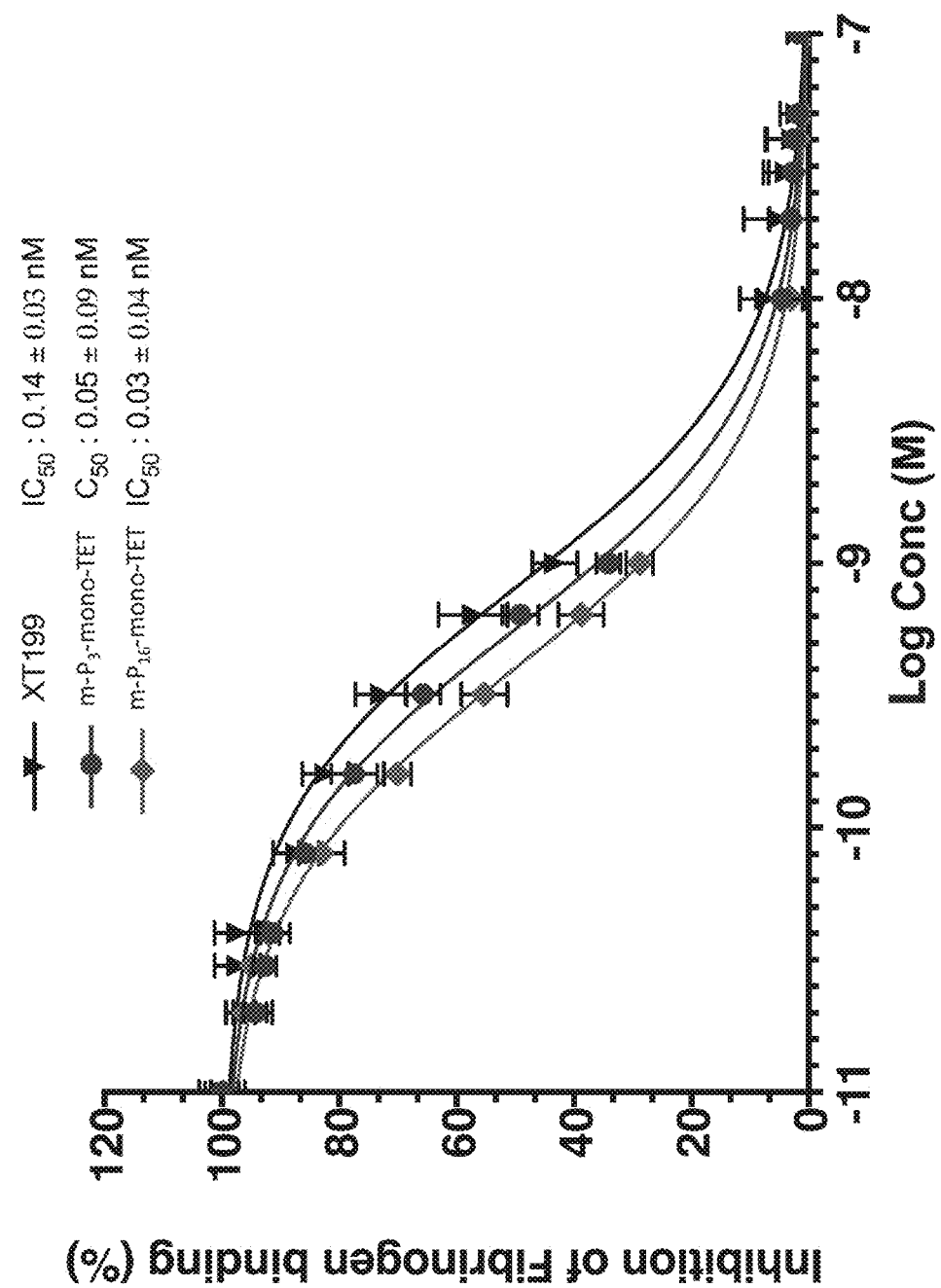
FIG. 11B depicts binding affinity of exemplary compounds and a reference compound in accordance with an embodiment of the invention.

Further, FIG. 11B shows binding affinity for additional test compounds m-P-mono-TET (n=3) and m-P-mono-TET (n=16) compared with XT199. Again, these compounds show high binding affinity, for example, 0.05±0.09 nM and 0.03±0.04 nM, respectively.

This high binding affinity is achieved by direct conjugation to the polymer (PEG) even without using a linker/Y moiety between the polymer and the thyrointegrin antagonist. For example, the direct conjugation does not require a Y moiety having an amine group as previously used. Further, the direct conjugation eliminates the need for click chemistry with such groups.

Molecules with high affinity for the αvβ3 integrin receptor typically share the pharmacophore of the RGD peptide, for example:

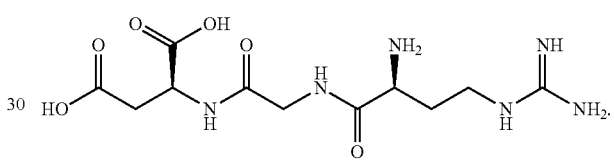

This structure has both a carboxylic acid group (far left section) and a multivalent nitrogen group, in this case a guanidine with 3 nitrogen atoms surrounding a single carbon atom (far right section). The carboxylic acid and multivalent nitrogen functional groups need to be a specific distance apart for high integrin αvβ3 affinity, typically approximately 14 angstroms, and it has been widely assumed in the conventional art that these two functional groups, separated by the required 14 angstroms, are critical for high integrin αvβ3 affinity.

This requirement has been exploited in the design of peptidomimetic integrin αvβ3 antagonists, examples of which include the following compounds:

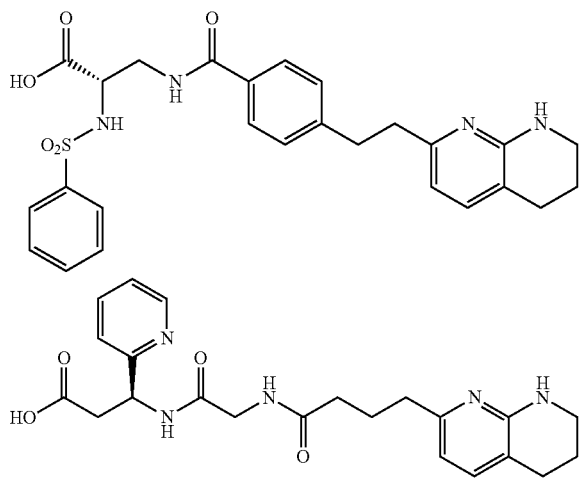

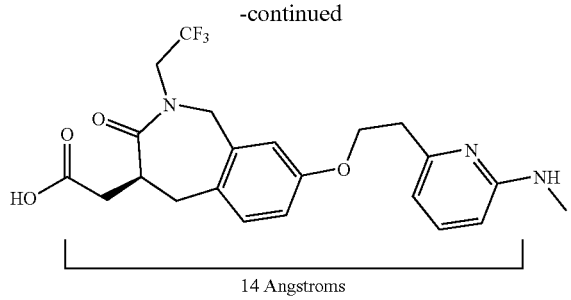

14 Angstroms from Feuston et. al., J. Med Chem. 2002, 45, 5640-5648. These peptidomimetics retain the carboxylic acid and multivalent nitrogen functionalities, separated by approximately 14 angstroms, with an amidine functional group (2 nitrogens surrounding a single carbon atom) instead of a guanidine. Thyromimetics with high integrin αvβ3 affinity have also recently been reported, for example in U.S. Pat. Nos. 10,201,616 and 10,961,204, both incorporated by reference above. The structures in each of these patents retain the carboxylic acid and multivalent nitrogen functionalities with the proper 14 angstrom separation, for example, with a 1,2,3-triazole as the multivalent nitrogen functional group. Further, there are many other examples of peptidometics using the template of a carboxylic acid and multivalent nitrogen groups with appropriate separation likely thousands of examples. While most integrin αvβ3 peptidometics follow this template, there is an example of an αvβ3 antagonist that does not have the multivalent nitrogen functionality (for example the following compound from Elliot et al, *Bioorganic and Medicinal Chemistry Letters*, 2009, 4832-4835):

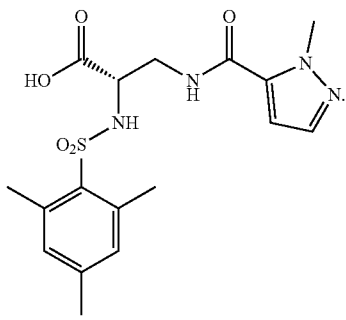 [SMILES: Cc1cc(C)c(S(=O)(=O)N[C@@H](CNC(=O)c2ccnn2C)C(=O)O)c(C)c1]

However, this compound does not have high binding affinity for integrin αvβ3, for example, a binding affinity of 11 nM, compared with 0.13±0.01 nM for XT199, 0.22±0.01 nM for P-bi-TET, 0.05±0.09 nM for m-P-mono-TET (n=3), 0.03±0.04 nM for m-P-mono-TET (n=16), and 0.27±0.02 nM for m-P-mono-TET (n=36). Thus, even this compound reinforces conventional understanding that the template of a carboxylic acid and multivalent nitrogen groups with appropriate separation of 14 angstroms is required/ideal for integrin αvβ3 activity.

Contrarily, in embodiments of the instant application, the multivalent nitrogen functional group can be eliminated with little to no loss of binding affinity and/or integrin αvβ3 activity as demonstrated by the disclosed binding affinities. The retention of proper activity is unexpected given the assumptions of the conventional art regarding the necessity of the two respective functional groups with appropriate separation.

Methods of Use/Treatment

As discussed above, the compounds and compositions described herein have good anti-angiogenic effect and may be used to treat conditions including but not limited to cancer. The anti-angiogenic effect and utility against cancer may be through binding with integrin αvβ3 as discussed above. Again, integrin αvβ3 regulates cell growth and survival, since ligation of this receptor can, under some circumstances, induce apoptosis in tumor cells. Disruption of cell adhesion with anti-αvβ3 antibodies, RGD peptides, and other integrin antagonists has been shown to slow tumor growth.

Anti-angiogenic effect and anti-tumor effect were further demonstrated using a Chorioallantoic membrane model (CAM)—Cancer Implant Model. The relative potency of the TET derivatives in the CAM cancer cell implant model of tumor weight was carried out as previously described by Marcinkiewicz, C., et al., *Obtustatin: a potent selective inhibitor of α1β1 integrin in vitro and angiogenesis in vivo*. Cancer Research, 2003. 63(9): p. 2020-2023 and Mousa, D. S., et al., *Nanoformulated bioactive compounds derived from different natural products combat pancreatic cancer cell proliferation*. International journal of nanomedicine, 2020. 15: p. 2259. Ten-day-old chick embryos were purchased from Charles River Avian Vaccine Services (Norwich, Conn., USA) and incubated at 37° C. with 55% relative humidity. A hypodermic needle was used to make a small hole was made on the shell at the air sac, and second hole was made on the broadside of the egg, directly over an avascular portion of the embryonic membrane that was identified by candling. A false air sac was created beneath the second hole by the application of negative pressure at the first hole, causing the CAM to separate the shell. A window approximately 1.0 cm$^2$ was cut in the shell over the dropped CAM using small craft grinding wheel (Dermal, Division of Emerson Electric Co. Racine, Wis., USA), allowing direct access to the underlying membrane.

Human Breast cancer (MDMBA 231), Skin (A375) and Ovarian (A2780) cells were grown in Dulbecco's Modified Eagle's Medium (DMEM) supplemented with 10% fetal bovine serum and 1% penicillin/streptomycin. Cells were cultured at 37° C. to sub-confluence and treated with 0.25% (w/v) trypsin/EDTA to induce cell release from flask. The cells were washed with culture medium and counted.

Cancer cells were seeded in 96-well plates (0.5 million cells per well) and were treated with compounds at different concentrations (1, 3, 10, 30 and 100 μg). At the end of the experiments, the cell cultures were supplemented with MTT reagent (3-(4,5-dimethylthiazol-2-yl)-2,5-diphenyltetrazolium bromide) and incubated for an additional 4 hours. Then, dimethyl sulfoxide (0.1% DMSO) was added to the cell culture to dissolve the formazan crystals and incubated for 10 minutes at room temperature. The absorbance rate of the cell cultures was read at 570 nm by using a Microplate Reader. All the reactions were performed in triplicate. Measured data of cellular proliferation were calculated using viability values of untreated control cells (100%).

Either MDMBA, A375 or A2780 cells at 1×10$^6$ cells in 30 μl of medium were mixed with same volume of Matrigel and implanted on the CAM. Treatments were applied: PBS, P-bi-TET (n=36), and m-P-mono-TET (n=36) (10 μg/CAM). The antitumor activities of the treatments on tumor angiogenesis and growth were determined 8 days after tumor cell implantation. MDMBA231, A375, and A2780 tumors were extracted by cutting tumors from the CAM and placing them in eppendorf tubes. Each tumor was weighed using an analytical balance. Data represented as mean tumor weights (mg)±SD per treatment group.

After incubation at 37° C. with 55% relative humidity for 3 days, the CAM tissue directly beneath each filter disk was resected from control and treated CAM samples. Tissues were washed 3 times with PBS, placed in 35-mm Petri dishes (Nalge Nunc, Rochester, N.Y., USA) and examined under an SV6 stereomicroscope (Karl Zeiss, Thornwood, N.Y., USA) at 50× magnification. Digital images of CAM sections exposed to filters were collected, using a 3-CCD color video camera system (Toshiba America, New York, USA), and analyzed with Image-Pro software (Media Cybernetics, Silver Spring, Md., USA). The numbers of vessel branch points contained in a circular region equal to the area of each filter disk were counted. One image was counted in each CAM preparation, and findings from 8 CAM preparations per group were analyzed for each treatment condition. Results are presented as mean tumor weight (mg) per treatment group (n=8 eggs per group). The effect of these treatments was determined after 7 days of implantation.

Figure 12:
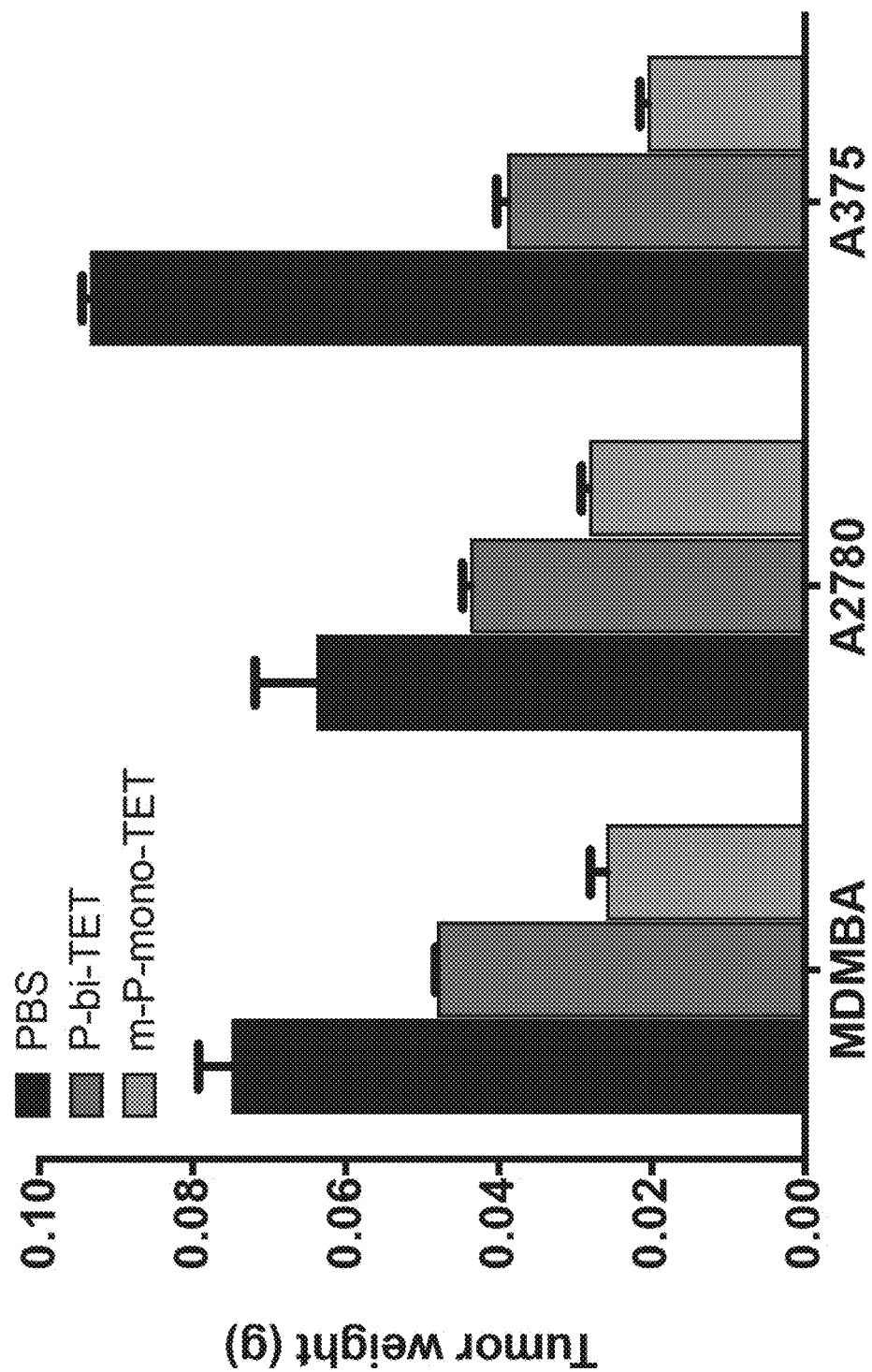
FIG. 12 depicts the effect of exemplary compounds on tumor weight in mice with breast (MDMBA), ovarian (A2780), and skin (A375) xenografts.

The results (mean tumor weight mg) is shown in FIG. 12. As shown in that figure both P-bi-TET (n=36) and m-P-mono-TET (n=36) showed reduction of tumor weight compared with the control group (PBS).

Figure 13:
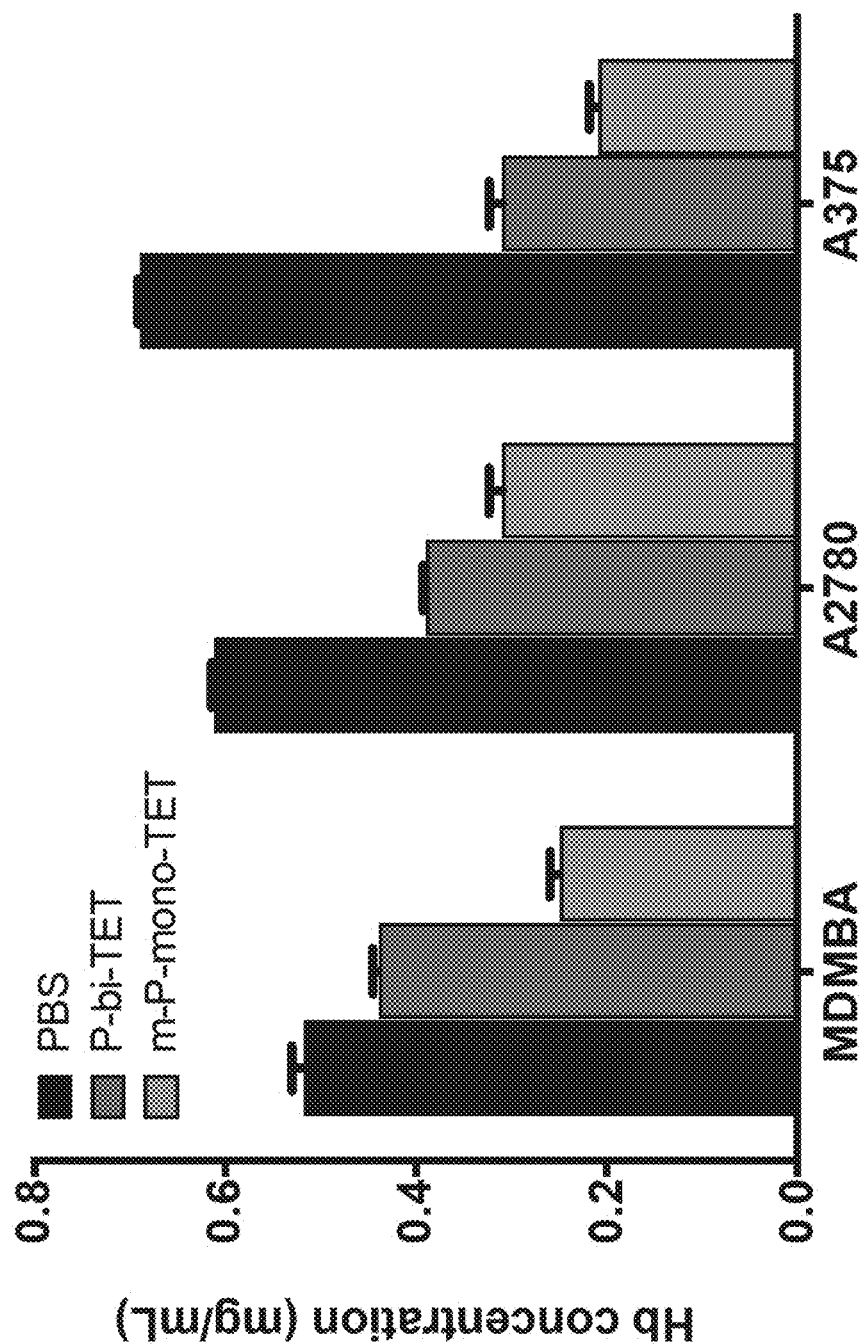
FIG. 13 depicts the effect of exemplary compounds on tumor hemoglobin concentration in mice with breast (MDMBA), ovarian (A2780), and skin (A375) xenografts.

Further, as shown in FIG. 13, tumor hemoglobin (Hb) content was indexed as a measure of tumor vascularity. Tumor sections were homogenized for 10 min in double distilled water and centrifugated at 2500 g for 10 min, and the supernatant was used for Hb analysis using Drabkin's reagent as described in Yalcin, M., et al., *Tetraiodothyroacetic acid (tetrac) and nanoparticulate tetrac arrest growth of medullary carcinoma of the thyroid*. The Journal of Clinical Endocrinology & Metabolism, 2010. 95(4): p. 1972-1980. Data are represented as tumor hemoglobin (mg/dL)±SD of the mean (n=5 per group) and are shown in FIG. 13. Again, both P-bi-TET (n=36) and m-P-mono-TET (n=36) showed reduction of tumor hemoglobin, and thus reduction of tumor vascularity, compared with the control group (PBS).

The efficacy of these compounds/compositions with respect exemplary tumors will now be described with reference to FIGS. 14-19. The study protocol is as follows:

Immunodeficient female NCr nude homozygous mice aged 5-6 weeks weighing 20-25 g were purchased from Taconic Biosciences, Inc (Germantown, N.Y., USA). All animal studies were conducted at the animal facility of the Veteran Affairs Medical Center (Albany, N.Y., USA) in accordance with approved institutional guidelines for humane animal treatment and according to the current guidelines. Mice were maintained under specific pathogen-free conditions and housed under controlled conditions of temperature (20-24° C.) and humidity (60-70%) and 12 hours light/dark cycle with ad libitum access to water and food. Mice were allowed to acclimatize for 5 days before the study.

For the subcutaneous (s.c.), the study was conducted where MDMBA231, A2780 and A375 cancer cells were harvested, suspended in 100 µL of DMEM with 50% Matrigel®, and 2-5×10⁶ cells were implanted s.c. dorsally in each flank to achieve two independent tumors per animal. Immediately prior to initiation of treatments, animals were randomized into treatment groups (5 animals/group) by tumor volume measurements with Vernier calipers. Treatments were begun after detection of palpable tumor mass (4-5 days post implantation). The treatments were control (PBS), P-bi-TET (n=36) (6 mg/kg), and m-P-mono-TET (n=36) (6 mg/kg). The agents were administered daily, s.c. for 21 days (ON Treatment) in one treatment arm, and in another treatment arm, were administrated daily for 21 days followed by 21 days discontinuation (ON Treatment+OFF Treatment). Animals were then humanely sacrificed, and tumors were harvested. Tumor weights and cell viability (bioluminescent signal intensity) were measured.

Tumor width and length were measured with calipers at 3 day intervals during ON and ON+OFF study and volumes were calculated using the standard formula $W \times L^2/2$. Tumor weight was measured of harvested lesions following animal sacrifice.

Figure 14:
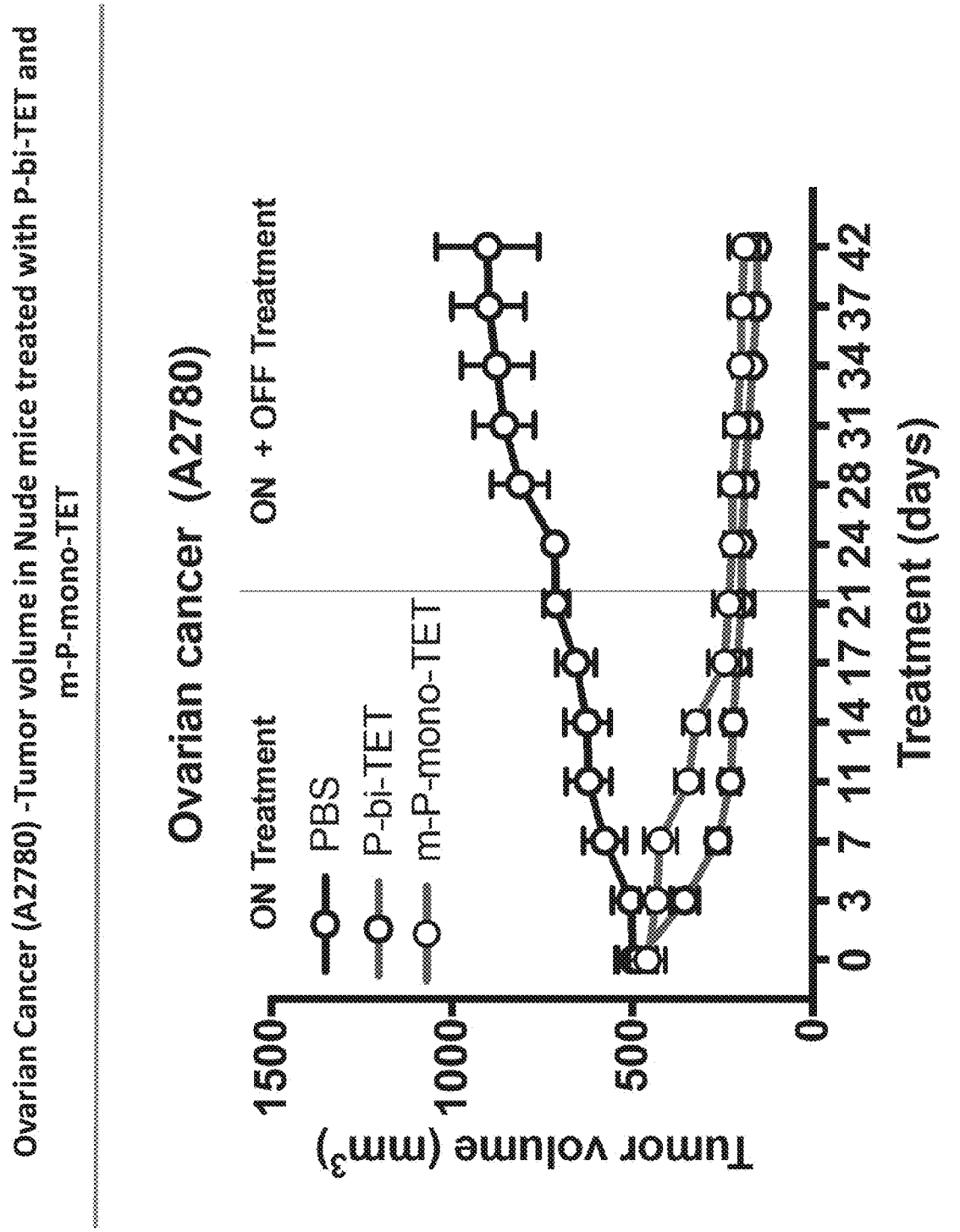
FIG. 14 depicts the effect of a 6 mg/kg dose of exemplary compounds on tumor volume in mice with ovarian (A2780) xenografts.

FIG. 14 shows tumor volume for ovarian cancer (A2780). As can be seen, both P-bi-TET and m-P-mono-TET showed reduction in tumor volume compared with the control (PBS). Further, the tumor volume was reduced both during the treatment period (ON Treatment) and for an additional 21 days following treatment (ON+OFF Treatment).

Figure 15:
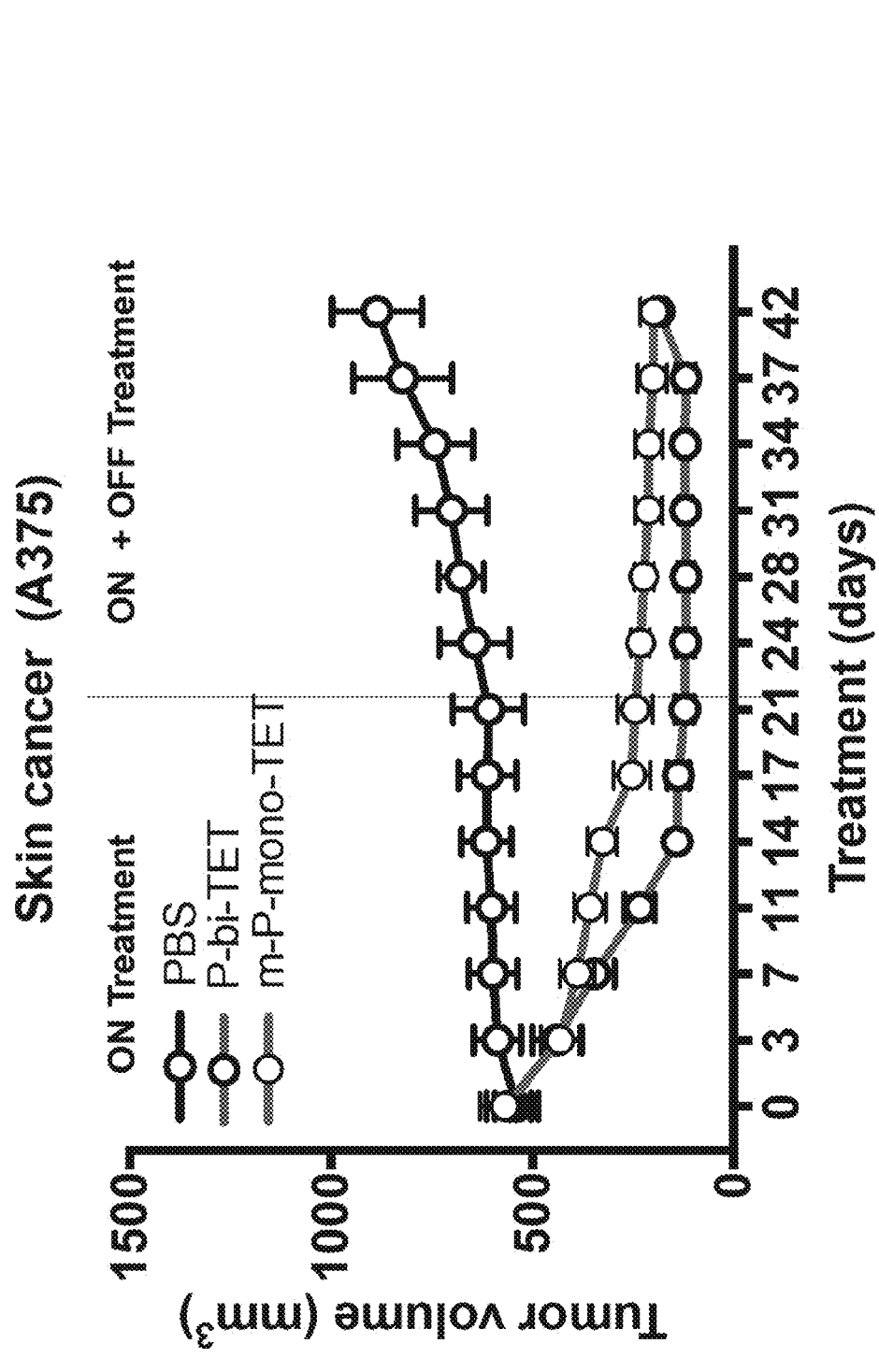
FIG. 15 depicts the effect of a 6 mg/kg dose of exemplary compounds on tumor volume in mice with skin (A375) xenografts.

FIG. 15 shows tumor volume for skin cancer (A375). As can be seen, both P-bi-TET and m-P-mono-TET showed reduction in tumor volume compared with the control (PBS). Further, the tumor volume was reduced both during the treatment period (ON Treatment) and for an additional 21 days following treatment (ON+OFF Treatment).

Figure 16:
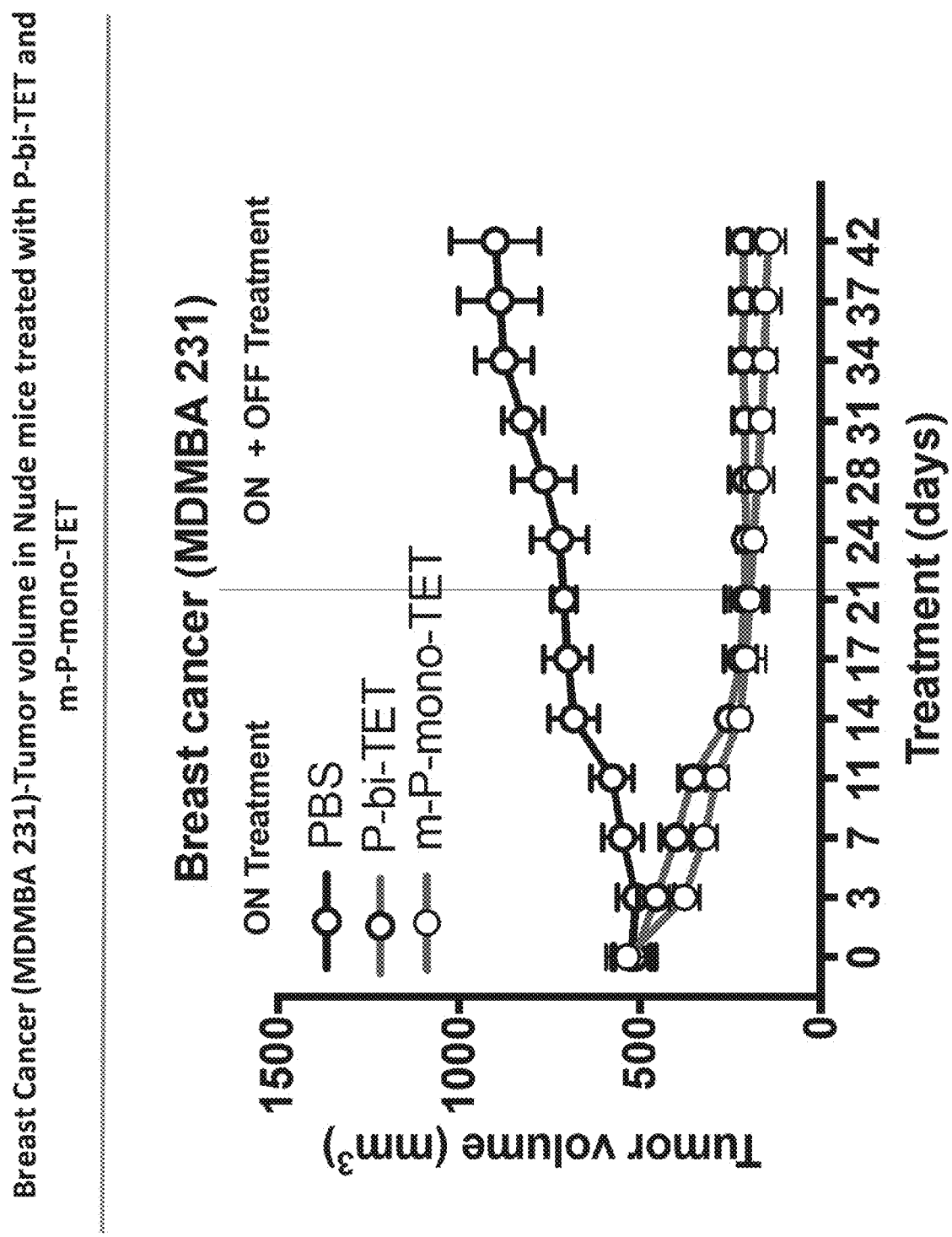
FIG. 16 depicts the effect of a 6 mg/kg dose of exemplary compounds on tumor volume in mice with breast (MDMBA 231) xenografts.

FIG. 16 shows tumor volume for breast cancer (MDMBA231). As can be seen, both P-bi-TET and m-P-mono-TET showed reduction in tumor volume compared with the control (PBS). Further, the tumor volume was reduced both during the treatment period (ON Treatment) and for an additional 21 days following treatment (ON+OFF Treatment).

Figure 17:
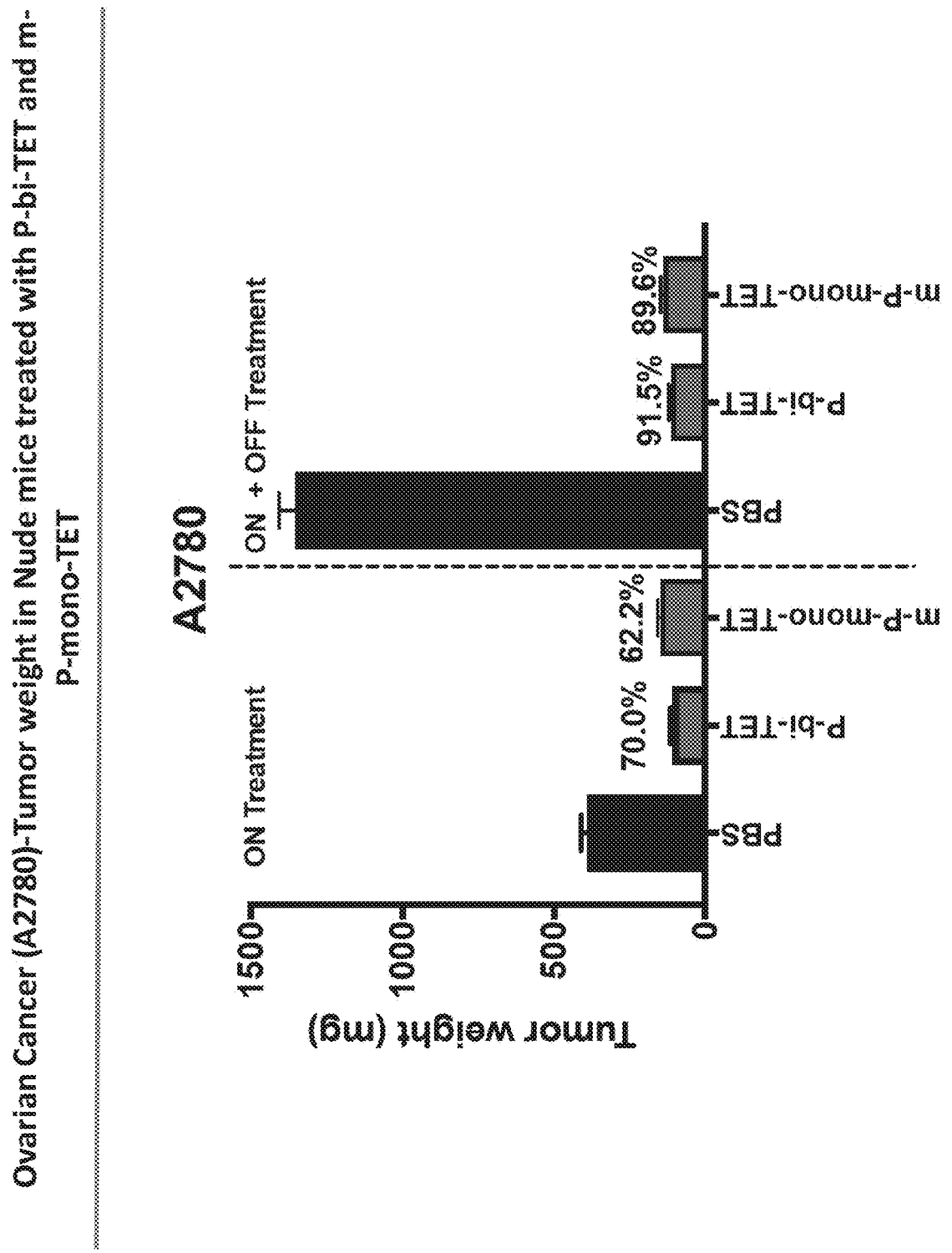
FIG. 17 depicts the effect of a 6 mg/kg dose of exemplary compounds on tumor weight in mice with ovarian (A2780) xenografts.

FIG. 17 shows tumor weight for ovarian cancer (A2780). As can be seen, both P-bi-TET and m-P-mono-TET showed reduction in tumor weight compared with the control (PBS). Further, the tumor weight was reduced during the treatment period (ON Treatment) and was further reduced when measured an additional 21 days following treatment (ON+OFF Treatment). Tumor weight was reduced by 91.5% (P-bi-TET) and 89.6% (m-P-mono-TET) 21 days after treatment (ON+OFF Treatment).

Figure 18:
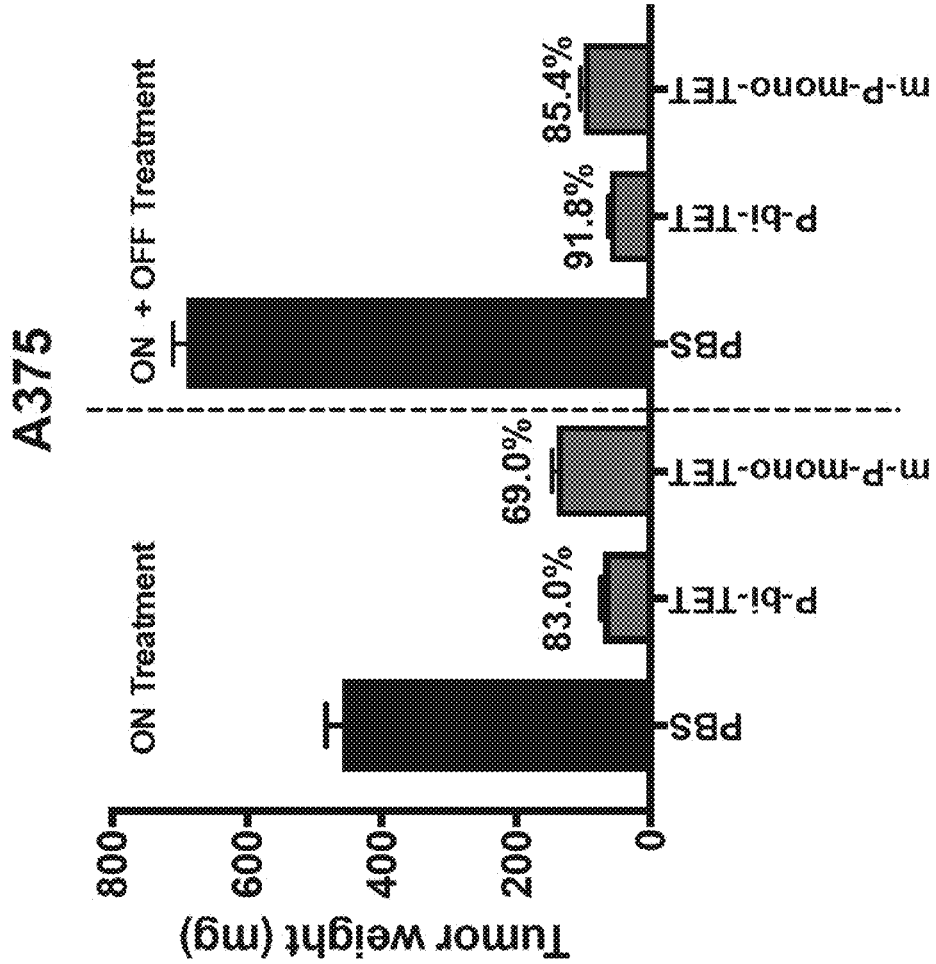
FIG. 18 depicts the effect of a 6 mg/kg dose of exemplary compounds on tumor volume in mice with skin (A375) xenografts.

FIG. 18 shows tumor weight for skin cancer (A375). As can be seen, both P-bi-TET and m-P-mono-TET showed reduction in tumor weight compared with the control (PBS). Further, the tumor weight was reduced during the treatment period (ON Treatment) and was further reduced when measured an additional 21 days following treatment (ON+OFF Treatment). Tumor weight was reduced by 91.8% (P-bi-TET) and 85.4% (m-P-mono-TET) 21 days after treatment (ON+OFF Treatment).

Figure 19:
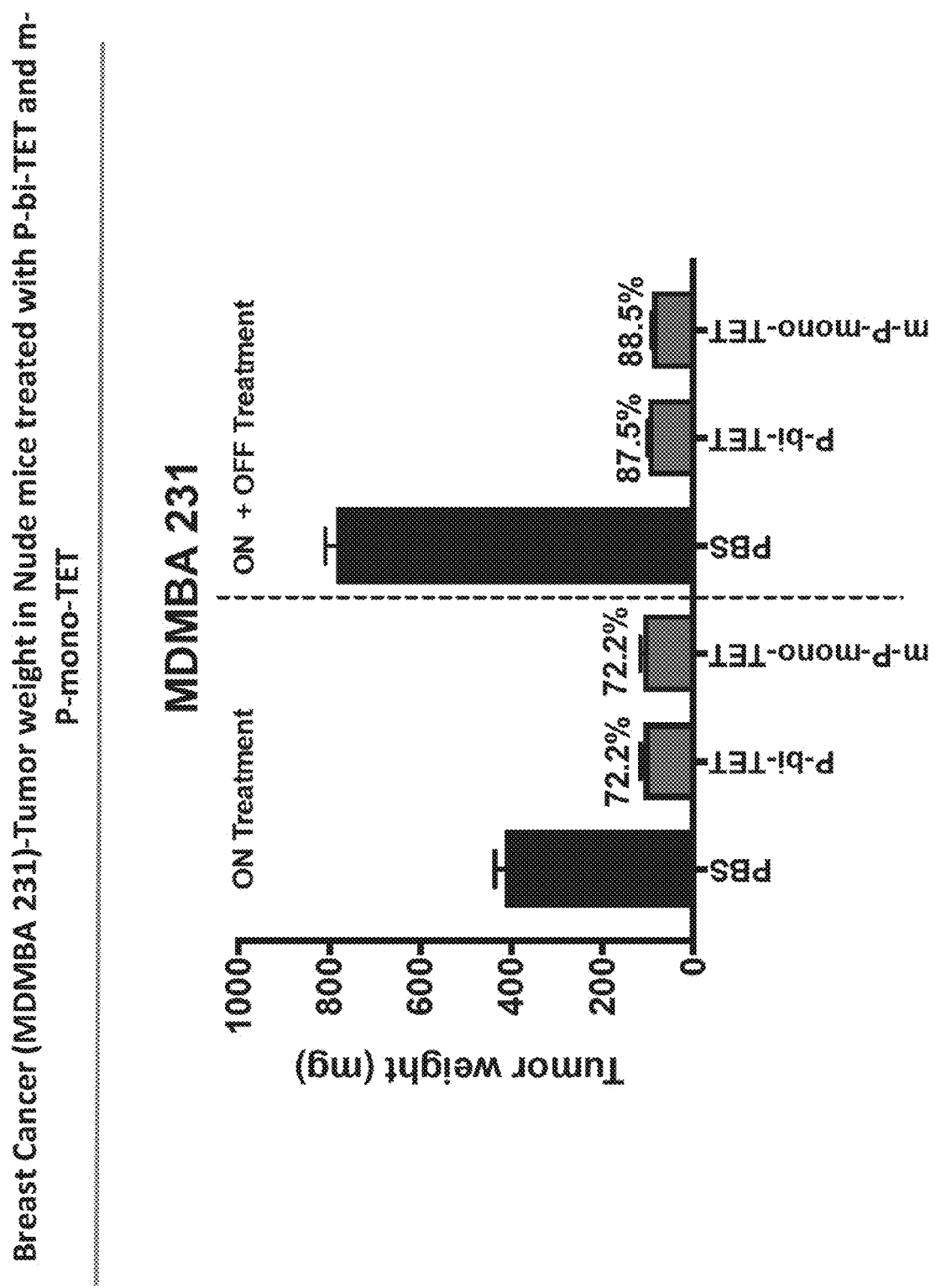
FIG. 19 depicts the effect of a 6 mg/kg dose of exemplary compounds on tumor volume in mice with breast (MDMBA 231) xenografts.

FIG. 19 shows tumor weight for breast cancer (MDMBA231). As can be seen, both P-bi-TET and m-P-mono-TET showed reduction in tumor weight compared with the control (PBS). Further, the tumor weight was reduced during the treatment period (ON Treatment) and was further reduced when measured an additional 21 days following treatment (ON+OFF Treatment). Tumor weight was reduced by 87.5% (P-bi-TET) and 88.5% (m-P-mono-TET) 21 days after treatment (ON+OFF Treatment).

Anti-tumor effect was also evaluated by histopathology. The tumors were fixed in 10% formalin and placed in cassettes and dehydrated using an automated tissue processor. The processed tissues were embedded in paraffin wax and the blocks trimmed and sectioned to about 5×5×4 µm size using a microtome. The tissue sections were mounted on glass slides using a hot plate and subsequently treated in the order of 100%, 90%, and 70% ethanol for 2 minutes.

Finally, the tissue sections were rinsed with water, stained with Harris's hematoxylin and eosin (H &E), and examined under a light microscope.

Figure 20:
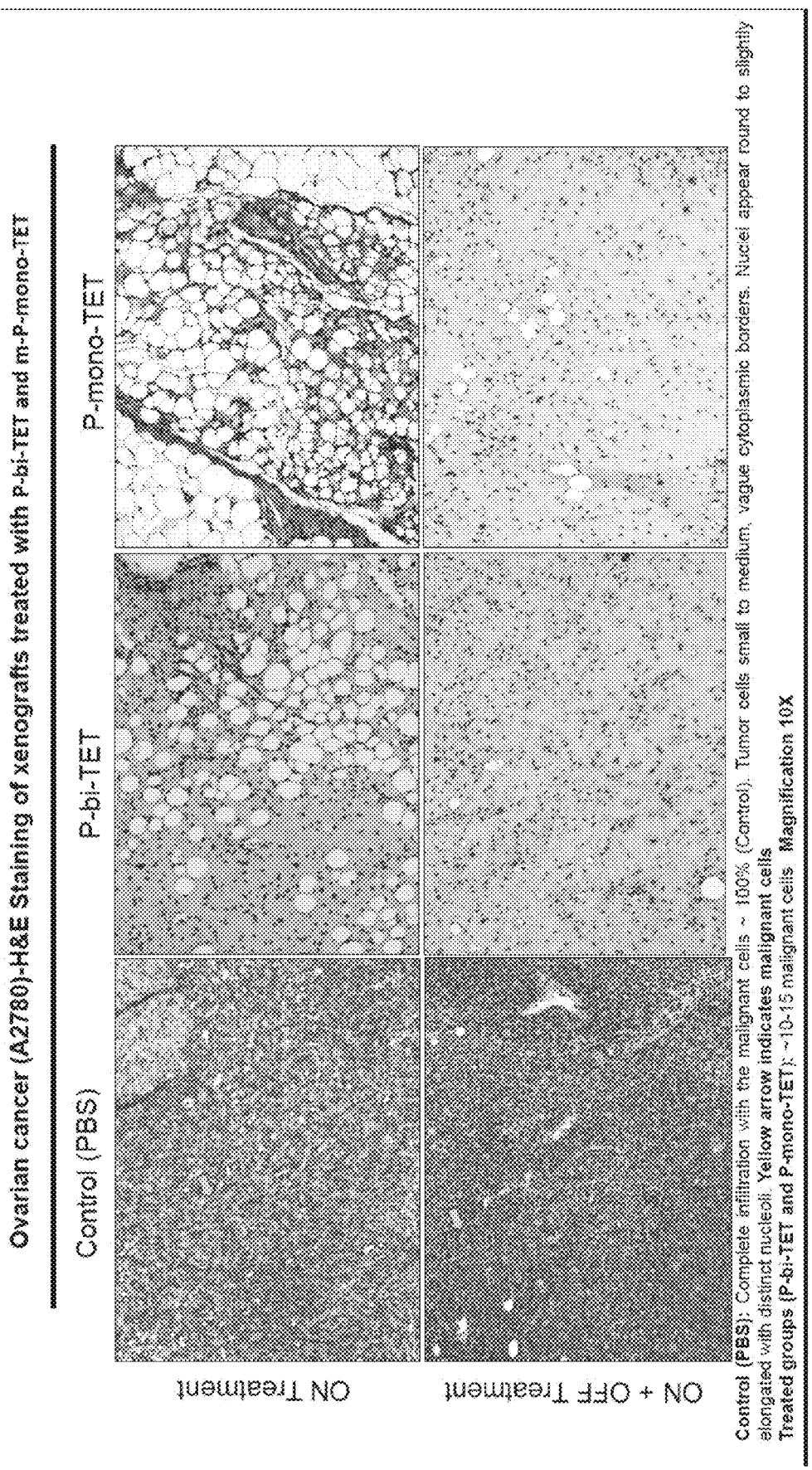
FIG. 20 shows staining of treated ovarian cancer (A2780) xenografts.
Figure 21:
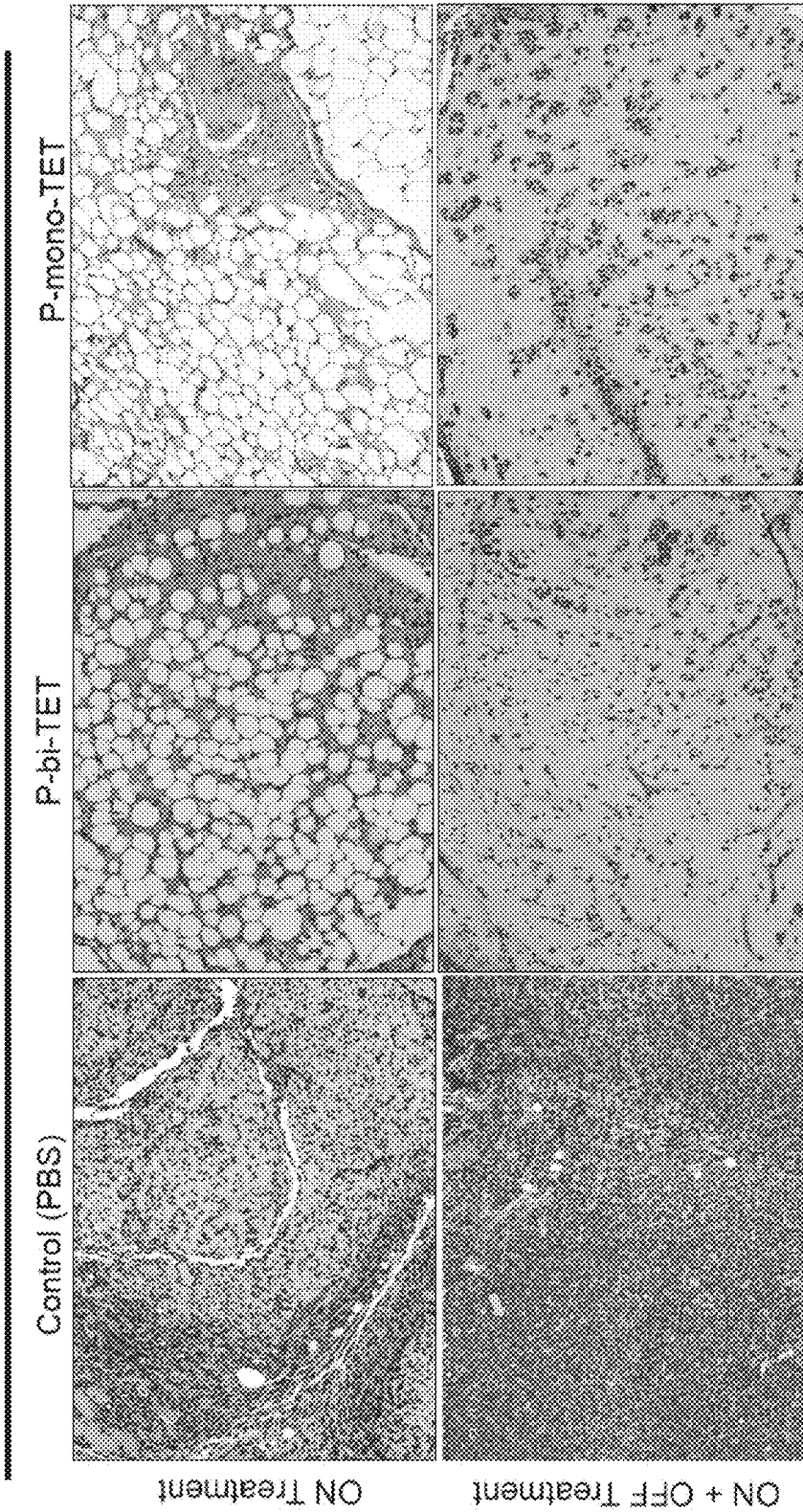
FIG. 21 shows staining of treated skin cancer (A375) xenografts.
Figure 22:
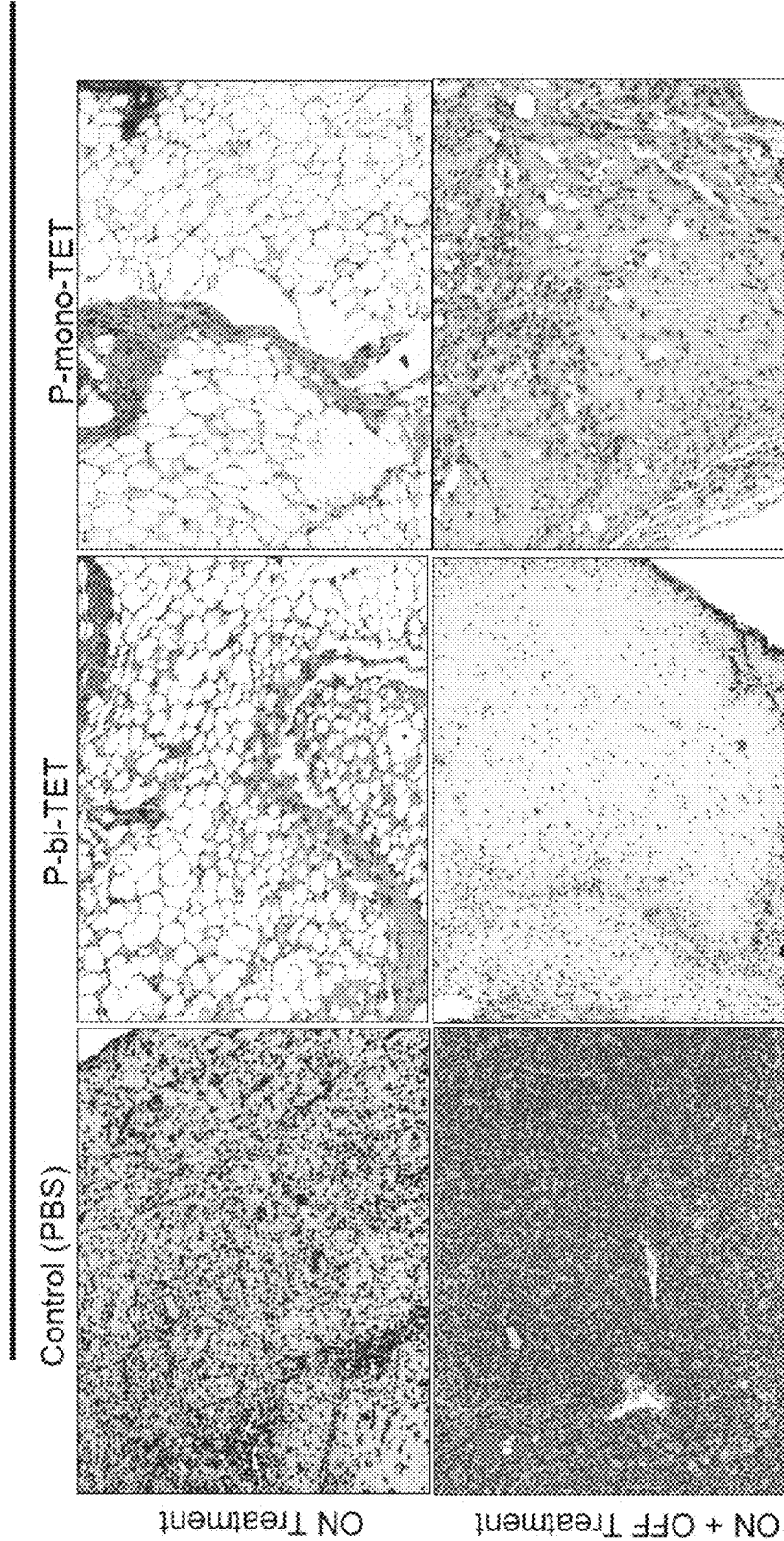
FIG. 22 shows staining of treated breast cancer (MDMBA231) xenografts.

FIG. 20 shows staining of treated ovarian cancer (A2780) xenografts. FIG. 21 shows staining of treated skin cancer (A375) xenografts. FIG. 22 shows staining of treated breast cancer (MDMBA231) xenografts. As shown in these Figures, the treatment groups showed high levels of necrotic cancer cells compared with viable tumor cells. In fact, the treatment arms having 21 days On Treatment showed 85% necrosis while the treatment arms having 21 days On Treatment followed by 21 days Off Treatment showed greater than 95% necrosis.

As demonstrated in these studies and shown in these Figures, the described compounds have therapeutic effect against various tumors, including but not limited to, ovarian, skin, and breast cancer tumors. The compounds may also be prepared as compositions comprising the disclosed compounds. Further, the compounds and/or the compositions may be used to treat conditions such as cancer by administering a therapeutically effective amount of the compound and/or composition to a patient in need thereof, for example, a patient suffering from the condition.

The compositions may also be used for imaging of cancer cell/tumors. For example, the compositions described herein may be used to image tumors using a dye or other means. Imaging may be desirable for diagnosis and/or for treatment monitoring. Moreover, the compositions may be used for simultaneous treatment and imaging. For example, the compositions may demonstrate increased retention in the targeted cancer cells/tumors, allowing for enhanced treatment.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A compound having a general formula

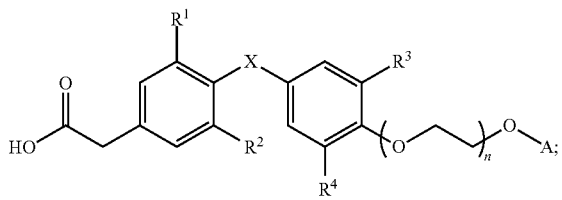

wherein $R^1$, $R^2$, $R^3$ and $R^4$ are each independently selected from the group consisting of hydrogen, iodine, linear alkanes, and branched alkanes;
X is oxygen (O) or sulfur (S);
n=3-72; and
A is selected from the group consisting of: H, a C1-C10 alkyl, a C4-C7 cycloalkyl, a C4-C7 cycloalkyl substituted with one of F, Cl, Br, I, CN, $CF_3$, $OCF_3$, $SO_2Me$, $NO_2$, a benzyl group, a substituted benzyl, a phenyl group, and a substituted phenyl.

2. The compound of claim 1, having a general formula:

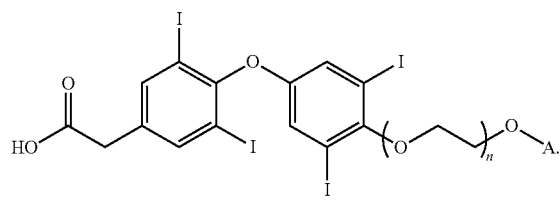

3. The compound of claim 1, wherein the compound is selected from the group consisting of:

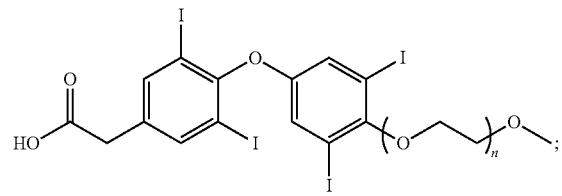

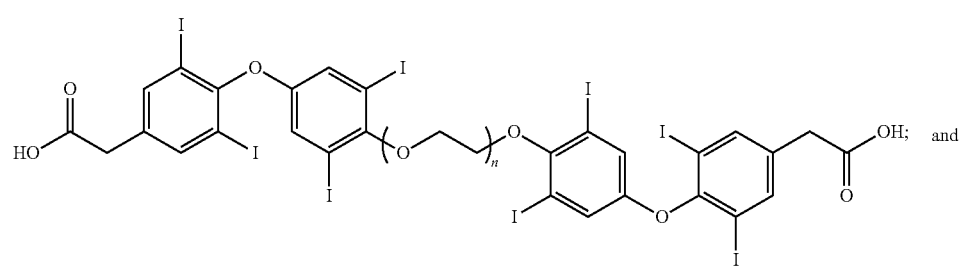

-continued

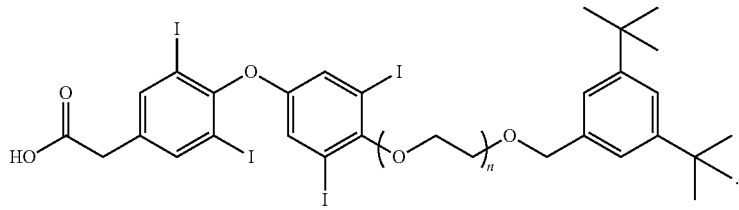

4. The compound of claim 1, wherein the compound has a general formula:

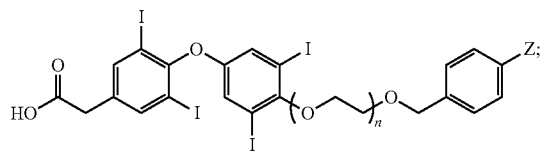

wherein Z is a halogen.

5. The compound of claim 4, wherein the compound has a general formula:

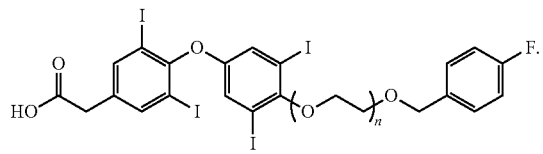

6. The compound of claim 1, wherein the compound comprises a dye for imaging.

7. A compound having a general formula:

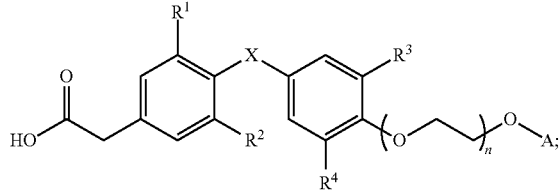

wherein $R^1$, $R^2$, $R^3$ and $R^4$ are each independently selected from the group consisting of hydrogen, iodine, linear alkanes, and branched alkanes;

X is oxygen (O) or sulfur (S);

n=3-72; and

A is selected from the group consisting of: H, a C1-C10 alkyl optionally substituted with one or more of F, Cl, Br, I, CN, CF3, SO2Me, NO2, CH2N=C(NH2)2, a C4-C7 cycloalkyl optionally substituted with one or more of F, Cl, Br, I, CN, CF3, SO2Me, NO2, CH2N=C(NH2)2, a benzyl group optionally substituted with one or more of F, Cl, Br, I, CN, CF3, SO2Me, NO2, CH2N=C(NH2)2, C1-C5 alkyl, a phenyl group optionally substituted with one or more of F, Cl, Br, I, CN, CF3, SO2Me, NO2, CH2N=C(NH2)2, C1-C5 alkyl, and

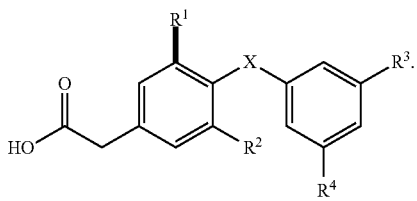

8. The compound of claim 7, having a general formula:

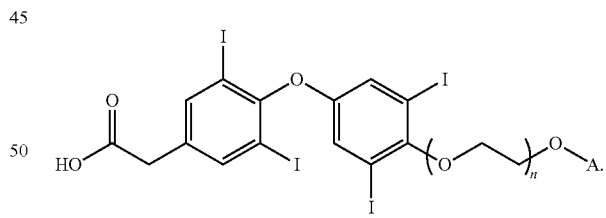

9. The compound of claim 7, wherein the compound is selected from the group consisting of:

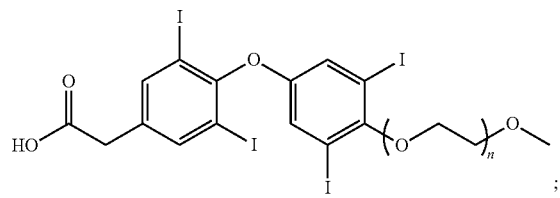

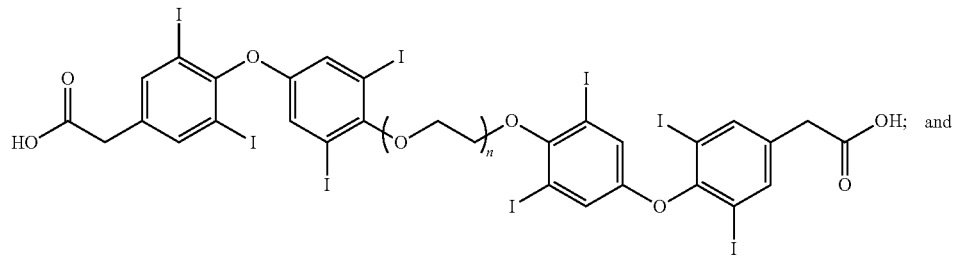

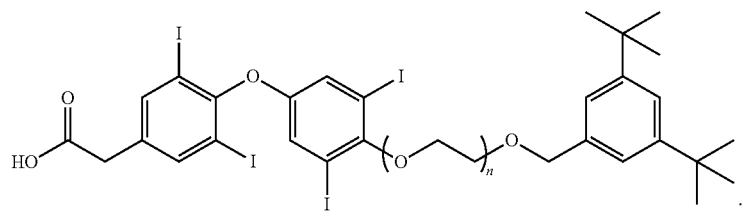

10. The compound of claim 7, wherein the compound has a general formula:

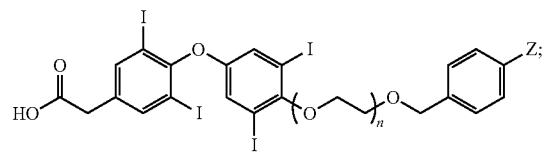

wherein Z is a halogen.

11. The compound of claim 10, wherein the compound has a general formula:

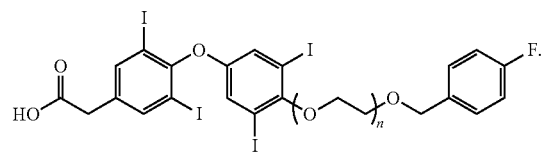

12. A method of treating a condition, wherein the condition is selected from skin cancer, ovarian cancer, breast cancer, rosacea, psoriasis, or poikiloderma, the method comprising:

providing a compound having a general formula:

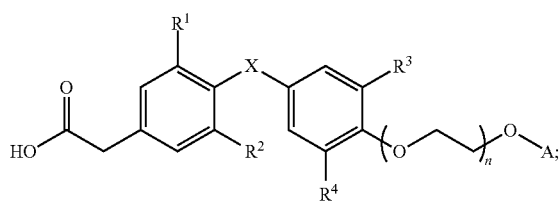

wherein $R^1$, $R^2$, $R^3$ and $R^4$ are each independently selected from the group consisting of hydrogen, iodine, linear alkanes, and branched alkanes;

X is oxygen (O) or sulfur (S);

n=3-72; and wherein A is selected from the group consisting of: H, a C1-C10 alkyl optionally substituted with one or more of F, Cl, Br, I, CN, CF3, SO2Me, NO2, CH2N=C(NH2)2, a C4-C7 cycloalkyl optionally substituted with one or more of F, Cl, Br, I, CN, CF3, SO2Me, NO2, CH2N=C(NH2)2, a benzyl group optionally substituted with one or more of F, Cl, Br, I, CN, CF3, SO2Me, NO2, CH2N=C(NH2)2, C1-C5 alkyl, a phenyl group optionally substituted with one or more of F, Cl, Br, I, CN, CF3, SO2Me, NO2, CH2N=C(NH2)2, C1-C5 alkyl, and

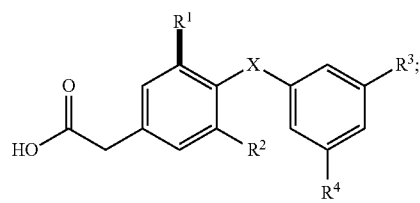

and administering a therapeutically effective amount of the compound to a patient in need thereof.

13. The method of claim 12, wherein the compound is selected from the group consisting of:
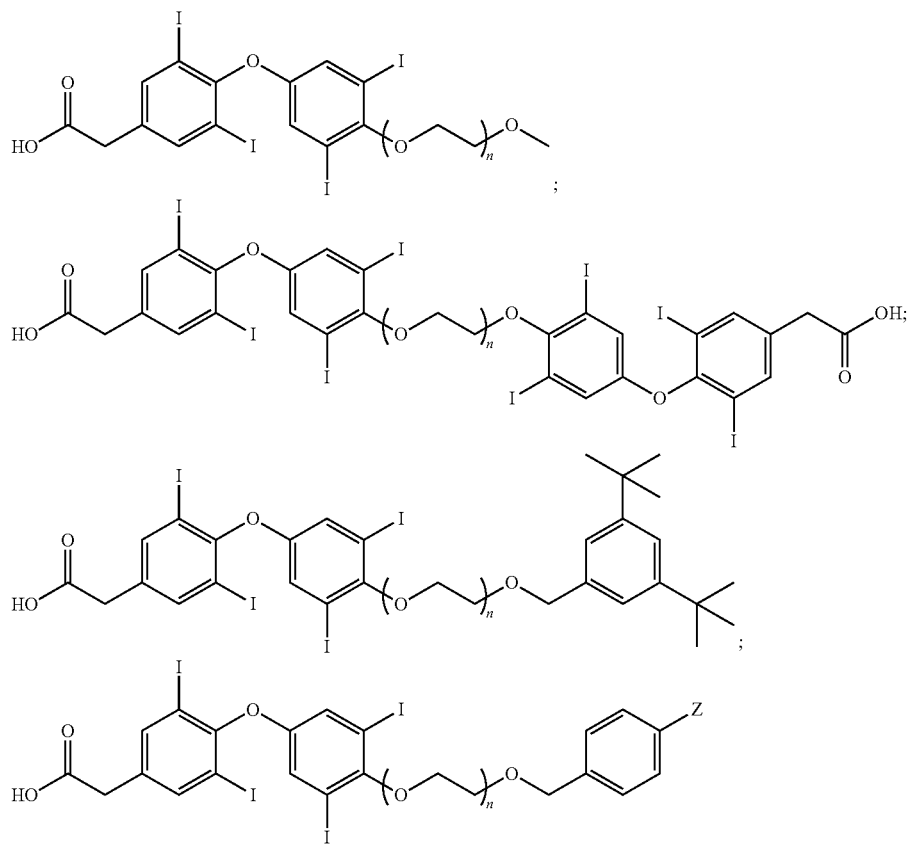
wherein Z is a halogen; and
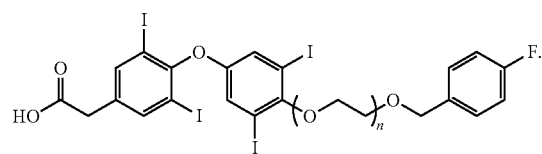
* * * * *